United States Patent [19]

Szczepanski et al.

[11] Patent Number: 5,679,623
[45] Date of Patent: Oct. 21, 1997

[54] IMIDAZOLE DERIVATIVES

[75] Inventors: Henry Szczepanski, Wallbach; Haukur Kristinsson, Bottmingen, both of Switzerland

[73] Assignee: Ciba-Geigy Corporation, Tarrytown, N.Y.

[21] Appl. No.: 460,473

[22] Filed: Jun. 2, 1995

Related U.S. Application Data

[62] Division of Ser. No. 172,369, Dec. 21, 1993, abandoned.

[30] Foreign Application Priority Data

Dec. 23, 1992 [CH] Switzerland .............................. 3946/92

[51] Int. Cl.$^6$ ...................... C07D 401/12; C07D 233/36; C07D 213/36
[52] U.S. Cl. .............................. 504/253; 504/275; 504/237; 504/236; 504/235; 504/261; 504/270; 504/266; 504/272; 504/262; 504/263; 504/265; 546/274.4; 544/333; 544/238; 544/405; 548/311.1; 548/202; 548/304.7; 548/215; 548/255; 548/127; 548/131
[58] Field of Search .................... 546/274.4; 504/253, 504/275, 237, 236, 235, 261, 270, 266, 272, 262, 263, 265; 548/311.1, 202, 304.7, 254, 215, 255, 127, 131; 544/333, 238, 405

[56] References Cited

U.S. PATENT DOCUMENTS

| | | | |
|---|---|---|---|
| 4,743,685 | 5/1988 | Brever et al. | 540/363 |
| 4,891,374 | 1/1990 | Thorwart et al. | |
| 4,931,439 | 6/1990 | Kristinssor | 514/242 |
| 4,996,325 | 2/1991 | Kristinssor | 548/132 |
| 5,179,094 | 1/1993 | Kristiansen et al. | 514/242 |
| 5,324,842 | 6/1994 | Beriger et al. | 548/132 |

FOREIGN PATENT DOCUMENTS

| | | |
|---|---|---|
| 0280868 | 9/1988 | European Pat. Off. |
| 2181130 | 4/1987 | United Kingdom. |

OTHER PUBLICATIONS

Monatshefte für Chemie, 108, pp. 665–680 (1977).
Journal of Medicinal Chemistry, vol. 18 (5), pp. 524–526 (1975).
J. Heterocycl. Chem., 29(5), 1081–4 (1992) and 28(6) 1511–16 (1991).

*Primary Examiner*—C. Warren Ivy
*Assistant Examiner*—D. Margaret M. Mach
*Attorney, Agent, or Firm*—Marla J. Mathias; William A. Teoli, Jr.

[57] ABSTRACT

Compounds of the formula

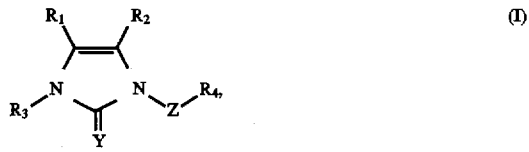

(I)

in which $R_1$, $R_2$, $R_3$, $R_4$, Y and Z are as defined in claim 1, and, if appropriate, the tautomers thereof, in each case in free form or in salt form, can be used as agrochemical active ingredients and can be prepared in a manner known per se.

13 Claims, No Drawings

IMIDAZOLE DERIVATIVES

This is a divisional of Ser. No. 08/172,369, filed Dec. 21, 1993 now abandoned.

The invention relates to compounds of the formula

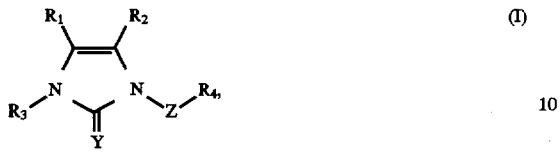

in which $R_1$ and $R_2$, independently of one another, are hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, or unsubstituted or mono-, di- or tri-substituted $C_3$–$C_6$cycloalkyl, substituents being selected from the group consisting of halogen and $C_1$–$C_3$alkyl;

$R_3$ is hydrogen, halo-$C_1$–$C_5$alkyl, N-$C_1$–$C_5$alkyl-N-$C_1$–$C_5$alkoxy-aminocarbonyl, unsubstituted or mono-, di- or tri-substituted $C_1$–$C_5$alkyl, substituents being selected from the group consisting of cyano, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, C(=O)OR$_6$, C(=O)N(R$_7$)R$_8$, C(=O)R$_9$, C(=O)SR$_{10}$, N(R$_{11}$)R$_{12}$, N=C(H)R$_{13}$ or mono-substituted $C_1$–$C_5$alkyl, the substituent being selected from the group consisting of C(=O)OR$_6$, C(=O)N(R$_7$)R$_8$, C(=O)R$_9$, C(=O)SR$_{10}$, N(R$_{11}$)R$_{12}$ and N=C(H)R$_{13}$;

$R_4$ is a monocyclic heterocyclic radical, which is unsubstituted or carries from 1 up to and including 3 substituents $R_5$, and where the basic ring structure of $R_4$ has 5 ring members of which from 1 up to and including 4 ring members are hetero atoms of which at least one is an N atom and the remaining hetero atoms, independently of one another, can be N, O or S atoms or has 6 ring members of which from 1 up to and including 4 ring members are N atoms or has 6 ring members of which 1 ring member is a group

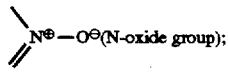

the substituents $R_5$, independently of one another, are halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl, mercapto or phenyl;

$R_6$, $R_7$, $R_8$, $R_9$, $R_{10}$ and $R_{11}$, independently of one another, are hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, or unsubstituted or mono-, di- or tri-substituted. $C_3$–$C_6$cycloalkyl, substituents being selected from the group consisting of halogen and $C_1$–$C_3$alkyl;

$R_{12}$ is hydrogen, substituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, unsubstituted or mono-, di- or tri-substituted phenyl, substituents being selected from the group consisting of halogen, $C_1$–$C_3$alkyl, $C_1$–$C_3$alkoxy, amino, $C_1$–$C_3$alkylamino, di($C_1$–$C_3$) alkylamino, $C_1$–$C_3$alkylthio, hydroxyl and mercapto, or unsubstituted or in the phenyl moiety mono-, di- or tri-substituted benzyl, substituents being selected from the group consisting of halogen, $C_1$–$C_3$alkyl, $C_1$–$C_3$alkoxy, amino, $C_1$–$C_3$alkylamino, di($C_1$–$C_3$) alkylamino, $C_1$–$C_3$alkylthio, hydroxyl and mercapto;

$R_{13}$ is unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, or an unsubstituted or mono-, di- or tri-substituted phenyl or pyridyl group, substituents being selected from the group consisting of halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl and mercapto;

Y is O, S or NR$_{14}$;

$R_{14}$ is hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, unsubstituted or mono-, di- or tri-substituted phenyl, substituents being selected from the group consisting of halogen, $C_1$–$C_3$alkyl, $C_1$–$C_3$alkoxy, amino, $C_1$–$C_3$alkylamino, di($C_1$–$C_3$) alkylamino, $C_1$–$C_3$alkylthio, hydroxyl and mercapto, or unsubstituted or in the phenyl moiety mono-, di- or tri-substituted benzyl, substituents being selected from the group consisting of halogen, $C_1$–$C_3$alkyl, $C_1$–$C_3$alkoxy, amino, $C_1$–$C_3$alkylamino, di($C_1$–$C_3$) alkylamino, $C_1$–$C_3$alkylthio, hydroxyl and mercapto; —Z—$R_4$ is —N=C($R_{15}$)—$R_4$ or —N($R_{16}$)—C(H)($R_{15}$)—$R_4$; and $R_{15}$ and $R_{16}$, independently of one another, are hydrogen or $C_1$–$C_5$alkyl, in free form or in salt form, and, if appropriate, to the tautomers thereof, in free form or in salt form, to a process for the preparation and to the use of these compounds and tautomers, to pesticidal compositions whose active ingredient is selected from these compounds and tautomers, in each case in free form or in the form of agrochemically utilisable salts, to a process for the preparation and to the use of these compositions, to plant propagation material treated with these compositions, to a method of controlling pests, to intermediates, in free form or in salt form, for the preparation of these compounds, and, if appropriate, to tautomers, in free form or in salt form, thereof, and to a process for the preparation and to the use of these intermediates.

Certain imidazole derivatives have been proposed in the literature as active ingredients in pesticides. However, the biological properties of these known compounds are not always entirely satisfactory in the field of pest control, resulting in a demand for other compounds with pesticidal properties, in particular for controlling insects and representatives of the order Acarina, this object being achieved according to the invention by providing the present compounds I.

Some of the compounds I can exist in the form of tautomers; for example, the compounds I, in which $R_3$ is hydrogen, can be in equilibrium with those tautomers which have a —N=C(YH)—N(Z$R_4$)— group instead of the —NH—C(=Y)—N(Z$R_4$)— group. Accordingly, the compounds I hereinabove and hereinafter are, where appropriate, also to be understood as meaning corresponding tautomers, even when no specific mention is made of the latter in each individual case.

Compounds I which have at least one basic center can form, for example, acid addition salts. These acid addition salts are formed, for example, with strong inorganic acids, such as mineral acids, for example perchloric acid, sulfuric acid, nitric acid, nitrous acid, a phosphoric acid or a hydrophilic acid, with strong organic carboxylic acids, such as unsubstituted or substituted, for example halogen-substituted, $C_1$–$C_4$alkanecarboxylic acids, for example acetic acid, or unsaturated or saturated dicarboxylic acids, for example oxalic acid, malonic acid, succinic acid, maleic acid, fumaric acid or phthalic acid, or hydroxycarboxylic acids, for example ascorbic acid, lactic acid, malic acid, tartaric acid or citric acid, or benzoic acid, or with organic sulfonic acids, such as unsubstituted or substituted, for example halogen-substituted, $C_1$–$C_4$alkane- or arylsulfonic acids, for example methane- or p-toluenesulfonic acid. Compounds I which have at least one acidic group can furthermore form salts with bases. Suitable salts with bases are, for example, metal salts such as alkali metal salts or alkaline earth metal salts, for example sodium salts, potassium salts or magnesium salts, or salts with ammonia or with an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Moreover, corresponding internal salts may also be formed, where possible. Preferred salts within the scope of the invention are agrochemically advantageous salts; however, the invention also comprises salts which are disadvantageous for agochemical purposes, for example salts which are toxic to honey bees or fish and which are employed, for example, for isolating or purifying free compounds I or agrochemically utilisable salts thereof. Due to the close relationship between the compounds I in free form and in the form of the salts thereof, the free compounds I, or the salts thereof, are to be understood analogously hereinabove and hereinafter as meaning, if appropriate, also the corresponding salts and the free compounds I, respectively. The same applies to tautomers of compounds I and salts thereof. Generally preferred is, in each case, the free form.

Unless otherwise defined, the general terms used hereinabove and hereinafter have the meanings given below.

Halogen, as a group per se and as structural element of other groups and compounds, such as haloalkyl, is fluorine, chlorine, bromine or iodine, in particular fluorine, chlorine or bromine, especially fluorine or chlorine.

Carbon-containing groups and compounds contain, unless otherwise defined, in each case 1 up to and including 5, preferably 1 up to and including 3, in particular 1 or 2, carbon atoms.

Cycloalkyl is cyclopropyl, cyclobutyl, cyclopentyl or cyclohexyl, preferably cyclopropyl.

Alkyl, as a group per se and as structural element of other groups and compounds, such as haloalkyl, alkoxy, alkylthio, alkylamino, dialkylamino and N-alkyl-N-alkoxy-aminocarbonyl, is, in each case with due consideration of the number of carbon atoms contained in each case in the particular group or compound, either straight-chain, i.e. methyl, ethyl, propyl, butyl or pentyl, or branched, for example isopropyl, isobutyl, sec-butyl, tert-butyl, isopentyl or neopentyl.

Alkenyl and alkynyl are straight-chain or branched and contain in each case two or, preferably, one unsaturated carbon-carbon bond(s). The double or triple bonds of these substituents are preferably separated from the remaining part of the compound I by at least one saturated carbon atom. Examples which may be mentioned are allyl, methallyl, but-2-enyl, but-3-enyl, propargyl, but-2-ynyl and but-3-ynyl.

Haloalkyl, can be partially halogenated or perhalogenated, where, in the case of a polyhalogenation, the halogen substituents can be identical or different. Examples of haloalkyl are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CF_2CFCl_2$, $CF_2CHBr_2$, $CF_2CHClF$, $CF_2CHBrF$ or $CClFCHClF$; propyl or isopropyl, each of which is mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$ or $CH(CF_3)_2$; and butyl or an isomer thereof, each of which can be mono- to nonasubstituted by fluorine, chlorine and/or bromine, such as $CF(CF_3)CHFCF_3$, $CF_2(CF_2)_2CF_3$ oder $CH_2(CF_2)_2CF_3$.

Preferred embodiments within the scope of the invention are:

(1) a compound of the formula I in which $R_1$ is hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, or unsubstituted or mono-, di- or tri-substituted $C_3$–$C_6$cycloalkyl, substituents being selected from the group consisting of halogen and $C_1$–$C_3$alkyl, especially hydrogen, unsubstituted or mono- or di-substituted $C_1$–$C_5$alkyl, substituents being selected from the group consisting of $C_1$–$C_3$alkoxy and $C_1$–$C_3$alkylthio, or unsubstituted $C_3$–$C_6$cycloalkyl, in particular hydrogen, unsubstituted $C_1$–$C_5$alkyl or unsubstituted cyclopropyl, especially tert-butyl or preferably methyl;

(2) a compound of the formula I in which $R_2$ is hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, or unsubstituted or mono-, di- or tri-substituted $C_3$–$C_6$cycloalkyl, substituents being selected from the group consisting of halogen and $C_1$–$C_3$alkyl, especially hydrogen, unsubstituted $C_1$–$C_5$alkyl or unsubstituted or mono- or di-substituted $C_2$–$C_5$alkenyl, substituents being selected from the group consisting of halogen, in particular hydrogen, unsubstituted $C_1$–$C_4$alkyl or unsubstituted or mono-substituted $C_3$–$C_4$alkenyl, substituents being selected from the group consisting of halogen, especially hydrogen;

(3) a compound of the formula I in which $R_3$ is hydrogen, halo-$C_1$–$C_5$alkyl, N-$C_1$–$C_5$alkyl-N-$C_1$–$C_5$alkoxy-aminocarbonyl, unsubstituted or mono-, di- or tri-substituted $C_1$–$C_5$alkyl, substituents being selected from the group consisting of cyano, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, $C(=O)OR_6$, $C(=O)N(R_7)R_8$, $C(=O)R_9$, $C(=O)SR_{10}$, $N(R_{11})R_{12}$, $N=C(H)R_{13}$ or mono-substituted $C_1$–$C_5$alkyl, the substituent being selected from the group consisting of $C(=O)OR_6$, $C(=O)N(R_7)R_8$, $C(=O)R_9$, $C(=O)SR_{10}$, $N(R_{11})R_{12}$ and $N=C(H)R_{13}$, where $R_6$, $R_7$, $R_8$, $R_9$, $R_{10}$, $R_{11}$, $R_{12}$ and $R_{13}$, in each case, have the meanings defined hereinbefore, especially hydrogen; halo-$C_1$–$C_5$alkyl; N-$C_1$–$C_5$alkyl-N-$C_1$–$C_5$alkoxy-aminocarbonyl; unsubstituted or mono-, di- or tri-substituted $C_1$–$C_5$alkyl, substituents being selected from the group consisting of cyano, $C_1$–$C_3$alkoxy and $C_1$–$C_3$alkylthio; unsubstituted or mono- or di-substituted $C_2$–$C_5$alkenyl, substituents being selected from the group consisting of halogen; unsubstituted $C_2$–$C_5$alkynyl; unsubstituted $C_3$–$C_6$cycloalkyl; $C(=O)OR_6$ wherein $R_6$ is unsubstituted $C_1$–$C_5$alkyl; $C(=O)N(R_7)R_8$ wherein $R_7$ and $R_8$, independently of one another, are unsubstituted $C_1$–$C_5$alkyl; $C(=O)R_9$ wherein $R_9$ is unsubstituted or mono- or di-substituted $C_1$–$C_5$alkyl, substituents being selected from the group consisting of $C_1$–$C_3$alkoxy; $N=C(H)R_{13}$ wherein $R_{13}$ is unsubstituted phenyl or unsubstituted pyridyl; or mono-substituted $C_1$–$C_5$alkyl, the substituent being selected from the group consisting of $C(=O)OR_6$ and $C(=O)R_9$ wherein $R_6$ and $R_9$ are unsubstituted $C_1$–$C_5$alkyl, in particular hydrogen; N—$C_1$–$C_2$alkyl-N—$C_1$–$C_2$alkoxy-aminocarbonyl; unsubstituted or mono- or di-substituted $C_1$–$C_5$alkyl, substituents being selected from the group consisting of cyano and $C_1$–$C_3$alkoxy; unsubstituted or mono-substituted $C_2$–$C_5$alkenyl, substituents being selected from the group consisting of halogen; unsubstituted $C_3$–$C_5$alkynyl; unsubstituted $C_3$–$C_5$cycloalkyl; $C(=O)OR_6$ wherein $R_6$ is unsubstituted $C_1$–$C_3$alkyl; $C(=O)N(R_7)R_8$ wherein $R_7$ and $R_8$, independently of one another, are unsubstituted $C_1$–$C_2$alkyl; $C(=O)R_9$ wherein $R_9$ is unsubstituted or mono-substituted $C_1$–$C_4$alkyl, substituents being selected from the group consisting of $C_1$–$C_2$alkoxy; or mono-substituted $C_1$–$C_5$alkyl, the substituent being selected from the group consisting of $C(=O)OR_6$ and $C(=O)R_9$ wherein $R_6$ and $R_9$ are unsubstituted $C_1$–$C_3$alkyl, especially hydrogen, unsubstituted $C_1$–$C_3$alkyl, preferably methyl, or preferably $C(=O)R_9$ wherein $R_9$ is unsubstituted $C_1$–$C_3$alkyl, preferably methyl;

(4) a compound of the formula I in which $R_4$ is a pyrrolyl, pyrazolyl, imidazolyl, thiazolyl, isothiazolyl, oxazolyl, isoxazolyl, triazolyl, oxadiazolyl, thiadiazolyl, tetrazolyl, pyrimidyl, pyrazinyl, pyridazinyl, triazinyl, tetrazinyl, pyridyl or 1-oxidopyridinio radical, which radical is unsubstituted or carries from 1 up to and including 3 substituents $R_5$, especially a pyridyl or 1-oxidopyridinio radical, which radical is unsubstituted or carries from 1 up to and including 2 substituents $R_5$, in particular an unsubstituted pyridyl radical;

(5) a compound of the formula I in which the substituents $R_5$, independently of one another, are halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl, mercapto or phenyl, especially halogen, $C_1$–$C_3$alkyl or phenyl;

(6) a compound of the formula I in which Y is O, S or $NR_{14}$, where $R_{14}$ has the meanings defined hereinbefore, especially O;

(7) a compound of the formula I in which

—Z—$R_4$ is —N=C($R_{15}$)—$R_4$ or —N($R_{16}$)—C(H)($R_{15}$)—$R_4$, where $R_4$, $R_{15}$ and $R_{16}$, in each case, have the meanings defined hereinbefore, especially —N=C(H)—$R_4$ or —N(H)—C(H)(H)—$R_4$, where $R_4$ has the meanings defined hereinbefore, in particular —N=C(H)—$R_4$, where $R_4$ has the meanings defined hereinbefore, especially —N=C(H)—$R_4$, where $R_4$ is pyrid-3-yl;

(8) a compound of the formula I in which $R_1$ is hydrogen, unsubstituted or mono- or di-substituted $C_1$–$C_5$alkyl, substituents being selected from the group consisting of $C_1$–$C_3$alkoxy and $C_1$–$C_3$alkylthio, or unsubstituted $C_3$–$C_6$cycloalkyl, $R_2$ is hydrogen, unsubstituted $C_1$–$C_5$alkyl or unsubstituted or mono- or di-substituted $C_2$–$C_5$alkenyl, substituents being selected from the group consisting of halogen, $R_3$ is hydrogen; halo-$C_1$–$C_5$alkyl; N—$C_1$–$C_5$alkyl-N—$C_1$–$C_5$alkoxy-aminocarbonyl; unsubstituted or mono-, di- or tri-substituted $C_1$–$C_5$alkyl, substituents being selected from the group consisting of cyano, $C_1$–$C_3$alkoxy and $C_1$–$C_3$alkylthio; unsubstituted or mono- or di-substituted $C_2$-$C_5$alkenyl, substituents being selected from the group consisting of halogen; unsubstituted $C_2$-$C_5$alkynyl; unsubstituted $C_3$-$C_6$cycloalkyl; $C(=O)OR_6$ wherein $R_6$ is unsubstituted $C_1$-$C_5$alkyl; $C(=O)N(R_7)R_8$ wherein $R_7$ and $R_8$, independently of one another, are unsubstituted $C_1$-$C_5$alkyl; $C(=O)R_9$ wherein $R_9$ is unsubstituted or mono- or di-substituted $C_1$-$C_5$alkyl, substituents being selected from the group consisting of $C_1$-$C_3$alkoxy; $N=C(H)R_{13}$ wherein $R_{13}$ is unsubstituted phenyl or unsubstituted pyridyl; or mono-substituted $C_1$-$C_5$alkyl, the substituent being selected from the group consisting of $C(=O)OR_6$ and $C(=O)R_9$ wherein $R_6$ and $R_9$ are unsubstituted $C_1$-$C_5$alkyl, $R_4$ is a pyridyl or 1-oxidopyridinio radical, which radical is unsubstituted or carries from 1 up to and including 2 substituents $R_5$, the substituents $R_5$, independently of one another, are halogen, $C_1$-$C_3$alkyl or phenyl;

Y is O; and

—Z—$R_4$ is —N=C(H)—$R_4$ or —N(H)—C(H)CH)—$R_4$, where $R_4$ has the meanings defined hereinbefore;

(9) a compound of the formula I in which $R_1$ is hydrogen, unsubstituted $C_1$-$C_5$alkyl or unsubstituted cyclopropyl;, $R_2$ is hydrogen, unsubstituted $C_1$-$C_4$alkyl or unsubstituted or mono-substituted $C_3$-$C_4$alkenyl, substituents being selected from the group consisting of halogen;

$R_3$ is hydrogen; N—$C_1$-$C_2$alkyl-N—$C_1$-$C_2$alkoxy-aminocarbonyl; unsubstituted or mono- or di-substituted $C_1$-$C_5$alkyl, substituents being selected from the group consisting of cyano and $C_1$-$C_3$alkoxy; unsubstituted or mono-substituted $C_2$-$C_5$alkenyl, substituents being selected from the group consisting of halogen; unsubstituted $C_3$-$C_5$alkynyl; unsubstituted $C_3$-$C_5$cycloalkyl; $C(=O)OR_6$ wherein $R_6$ is unsubstituted $C_1$-$C_3$alkyl; $C(=O)N(R_7)R_8$ wherein $R_7$ and $R_8$, independently of one another, are unsubstituted $C_1$-$C_2$alkyl; $C(=O)R_9$ wherein $R_9$ is unsubstituted or mono-substituted $C_1$-$C_4$alkyl, substituents being selected from the group consisting of $C_1$-$C_2$alkoxy; or mono-substituted $C_1$-$C_5$alkyl, the substituent being selected from the group consisting of $C(=O)OR_6$ and $C(=)R_9$ wherein $R_6$ and $R_9$ are unsubstituted $C_1$-$C_3$alkyl;

$R_4$ is an unsubstituted pyridyl radical;

Y is O; and

—Z—$R_4$ is —N=C(H)—$R_4$, where $R_4$ is unsubstituted pyrid-3-yl;

(10) a compound of the formula I in which $R_1$ is tert-butyl or preferably methyl;

$R_2$ is hydrogen;

$R_3$ is hydrogen, unsubstituted $C_1$-$C_3$alkyl, preferably methyl, or preferably $C(=O)R_9$ wherein $R_9$ is unsubstituted $C_1$-$C_3$alkyl, preferably methyl, $R_4$ is an unsubstituted pyridyl radical;

Y is O; and

—Z—$R_4$ is —N=C(H)—$R_4$, where $R_4$ is unsubstituted pyrid-3-yl;

in each case in free form or in salt form, and, if appropriate, in each case a tautomer thereof, in free form or in salt form.

Particularly preferred within the scope of the invention are the compounds of the formula I mentioned in Examples H8 to H16, in free form or in salt form.

Especially preferred within the scope of the invention is the compound of the formula I in which $R_1$ is methyl, $R_2$ is H, $R_3$ is $C(=O)CH_3$, Y is O, —Z—$R_4$ is —N=C(H)—$R_4$ and $R_4$ is unsubstituted pyrid-3-yl.

As another object of the invention, the process for the preparation of the compounds of the formula I or, if appropriate, the tautomers thereof, in each case in free form or in salt form, comprises, for example, a) to prepare a compound of the formula I, in which —Z—$R_4$ is —N=C($R_{15}$)—$R_4$, wherein $R_4$ and $R_{15}$ are as defined for formula I, or, if appropriate, a tautomer and/or salt thereof, reacting a compound of the formula

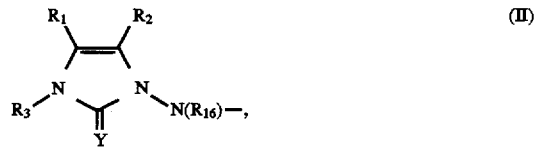

in which $R_1$, $R_2$, $R_3$ and Y are as defined for formula I and $R_{16}$ is hydrogen, or a tautomer and/or salt thereof with a compound of the formula

$$O=C(R_{15})—R_4 \quad (III),$$

which is known or can be prepared in analogy to corresponding known compounds, and in which $R_4$ and $R_{15}$ are as defined for formula I, or with a tautomer and/or salt thereof, preferably in the presence of an acid catalyst or a water-binding agent, or b) to prepare a compound of the formula I, in which —Z—$R_4$ is —N($R_{16}$)—C(H)($R_{15}$)—$R_4$, wherein $R_4$, $R_{15}$ and $R_{16}$ are as defined for formula I, or, if appropriate, a tautomer and/or salt thereof, reacting a compound of the formula II in which $R_1$, $R_2$, $R_3$, $R_{16}$ and Y are as defined for formula I, or a tautomer and/or salt thereof with a compound of the formula

$$X—C(H)(R_{15})—R_4 \quad (IV),$$

which is known or can be prepared in analogy to corresponding known compounds, and in which $R_4$ and $R_{15}$ are as defined for formula I and X is a leaving group, or with a tautomer and/or salt thereof, preferably in the presence of a base, and/or, if desired, converting a compound of the formula I or a tautomer thereof, in each case in free form or in salt form, which can be obtained according to the process or by a different method, into a different compound of the formula I or a tautomer thereof, separating an isomer mixture which can be obtained according to the process and isolating the desired isomer, and/or converting a free compound of the formula I or a tautomer thereof, which can be obtained according to the process or by a different method, into a salt, or converting a salt of a compound of the formula I or of a tautomer thereof, which can be obtained according to the process or by a different method, into the free compound of the formula I or into a tautomer thereof, or into a different salt What has been said hereinabove for tautomers and/or salts of compounds I applies analogously to staffing materials mentioned hereinabove and hereinafter with regard to the tautomer and/or salts thereof.

The reactions described hereinabove and hereinafter are carried out in a manner known per se, for example in the absence or, conventionally, in the presence of a suitable solvent or diluent or a mixture of these, the process being carried out, as required, with cooling, at room temperature or with heating, for example in a temperature range from approximately −80° C. to the boiling point of the reaction mixture, preferably from approximately −20° C. to approximately +150° C., and, if necessary, in a sealed container, under pressure, in an inert gas atmosphere and/or under anhydrous conditions. Particularly advantageous reaction conditions can be found in the examples.

The starting materials mentioned hereinabove and hereinafter which are used for the preparation of the compounds I or, if appropriate, of the tautomers thereof, in each case in free form or in salt form, are known or can be prepared by methods known per se, for example in accordance with the information given hereinafter.

Variant a):

Suitable acid catalysts for facilitating the reaction are, for example, those acids, employed in catalytic amounts, which have been mentioned hereinabove as being suitable for the formation of acid addition salts with compounds I, preferably mineral acids, such as sulfuric acid or, in particular, hydrochloric acid.

Suitable water-binding agents for facilitating the reaction are, for example, carbodiimides, such as N,N'-dicyclohexylcarbodiimide, or 1-alkyl-2-halo-pyridinium salts, such as 1-methyl-2-chloro-pyridinium iodide.

The reactants can be reacted with each other as such, i.e. without adding a solvent or diluent, for example in the molten state. However, in most cases it is advantageous to add an inert solvent or diluent or a mixture of these. The following may be mentioned as examples of such solvents or diluents: aromatic, aliphatic and alicyclic hydrocarbons and halohydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, ten-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide. If the reaction is carried out in the presence of an acid catalyst, then acids which are employed in excess, for example strong organic carboxylic acids, such as unsubstituted or substituted, for example halogen-substituted, $C_1$–$C_4$alkanecarboxylic acids, for example formic acid, acetic acid or propionic acid, can also act as solvents or diluents. Optionally, the solvents or diluents can be used in aqueous form, i.e. in the form of a mixture with water.

The reaction is advantageously carried out in a temperature range from approximately 0° C. to approximately +180° C., preferably from approximately +10° C. to approximately +130° C., in many cases in the range between room temperature and the reflux temperature of the reaction mixture.

If desired, the water of reaction, which is formed during the reaction, can be removed with the aid of a water separator, by azeotropic distillation or by adding a suitable molecular sieve.

Variant b):

Suitable leaving groups X in the compounds IV are, for example, hydroxyl, $C_1$–$C_8$alkoxy, halo-$C_1$–$C_8$alkoxy, $C_1$–$C_8$alkanoyloxy, mercapto, $C_1$–$C_8$alkylthio, halo-$C_1$–$C_8$alkylthio, $C_1$–$C_8$alkanesulfonyloxy, halo-$C_1$–$C_8$alkanesulfonyloxy, benzenesulfonyloxy, toluenesulfonyloxy and halogen.

Suitable bases for facilitating the detachment of HX are, for example, the hydroxides, hydrides, amides, alkanolates, acetates, carbonates, dialkylamides or alkylsilylamides of alkali metals or alkaline earth metals, alkylamines, alkylenediamines, free or N-alkylated, saturated or unsaturated cycloalkylamines, basic heterocycles, ammonium hydroxides and carbocyclic amines. Examples which may be mentioned are sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)-pyridine, quinuclidine, N-methylmorpholine, benzyltrimethylammoniumhydroxide and 1,5-diazabicyclo[5.4.0]undec-5-ene (DBU).

The reactants can be reacted with each other as such, i.e. without adding a solvent or diluent, for example in the molten state. However, in most eases it is advantageous to add an inert solvent or diluent or a mixture of these. The following may be mentioned as examples of such solvents or diluents: aromatic, aliphatic and alicyclic hydrocarbons and halohydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethane or tetrachloroethane; esters, such as ethyl acetate; ethers, such as diethyl ether, dipropyl ether, diisopropyl ether, dibutyl ether, ten-butyl methyl ether, ethylene glycol monoethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide. If the reaction is carried out in the presence of a base, then bases which are employed in excess, such as triethylamine, pyridine, N-methylmorpholine or N,N-diethylaniline, can also act as solvents or diluents. Optionally, the solvents or diluents can be used in aqueous form, i.e. in the form of a mixture with water.

The reaction is advantageously carried out in a temperature range from approximately 0° C. to approximately +180° C., preferably from approximately +10° C. to approximately +130° C., in many cases in the range between room temperature and the reflux temperature of the reaction mixture.

The compounds II and the tautomers thereof, in each case in free form or in salt form, which are employed as educts in process variants a) and b) are novel and also form part of the invention. Particularly preferred compounds within the scope of the invention are the compounds II mentioned in Examples H4 to H7.

The invention also relates to the process for the preparation of the compounds of the formula II or the tautomers thereof, in each case in free form or in salt form, which comprises, for example, c) solvolysing a compound of the formula

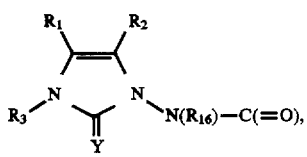
(V)

in which $R_1$, $R_2$, $R_3$, $R_{16}$ and Y are as defined for formula I and Q is $C_1$–$C_5$alkyl or halo-$C_1$–$C_5$alkyl, or a tautomer and/or salt thereof in the presence of a solvolysing agent, preferably in the presence of a solvent or diluent, and/or, if desired, converting a compound of the formula II or a tautomer thereof, in each case in free form or in salt form, which can be obtained according to the process or by a different method, into a different compound of the formula II or a tautomer thereof, separating an isomer mixture which can be obtained according to the process and isolating the desired isomer, and/or converting a free compound of the formula II or a tautomer thereof, which can be obtained according to the process or by a different method, into a salt, or converting a salt of a compound of the formula II or of a tautomer thereof, which can be obtained according to the process or by a different method, into the free compound of the formula II or into a tautomer thereof, or into a different salt.

Variant c):

Suitable solvolysing agents for the solvolysis of the compounds V are water, bases or, preferably, acid catalysts. Suitable bases are, for example, of the type given in variant b). Suitable acid catalysts are, for example, of the type given in variant a). Preferred as acid catalyst is gaseous hydrogen chloride.

The compound V and the solvolysing agent can be reacted with each other as such, i.e. without adding a solvent or diluent, for example in the molten state. However, in most cases it is advantageous to add an inert solvent or diluent or a mixture of these. Suitable solvents or diluents am, for example, of the type given under variants a) and b).

The reaction is advantageously carried out in a temperature range from approximately −20° C. to approximately +180° C., preferably from approximately +10° C. to approximately +100° C., in many cases in the range between room temperature and the reflux temperature of the reaction mixture.

In a preferred embodiment of process variant c), the compound II which is obtained is not isolated, but is reacted further in situ, in accordance with the procedure of process variant a), to give a compound I.

The compounds V and the tautomers thereof, in each case in free form or in salt form, which are employed as educts in process variant c) are novel and also form part of the invention. Particularly preferred compounds within the scope of the invention are the compounds V mentioned in Examples H2 and H3.

The invention also relates to the process for the preparation of the compounds of the formula V or the tautomers thereof, in each case in free form or in salt form, which comprises, for example, d) to prepare a compound of the formula V, in which $R_{16}$ is hydrogen, or, if appropriate, a tautomer and/or salt thereof, reacting a compound of the formula

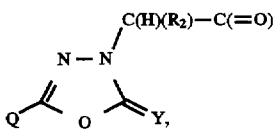
(VI)

which is known or can be prepared in analogy to corresponding known compounds, and in which $R_1$, $R_2$ and Y are as defined for formula I and Q is as defined for formula V, or a salt thereof with a compound of the formula $$R_3\text{—}NH_2 \qquad (VII),$$

which is known or can be prepared in analogy to corresponding known compounds, and in which $R_3$ is as defined for formula I, or with a salt thereof, preferably in the presence of a solvent or diluent, or e) to prepare a compound of the formula V, in which $R_{16}$ is other than hydrogen, or, if appropriate, a tautomer and/or salt thereof, reacting a compound of the formula V, in which $R_{16}$ is hydrogen, and which can be obtained, for example, according to variant d), or a tautomer and/or salt thereof with a compound of the formula $$R_{16}\text{—}X \qquad (VIII),$$

which is known or can be prepared in analogy to corresponding known compounds, and in which $R_{16}$ is as defined for formula I with the exception of hydrogen and X is a leaving group, preferably in the presence of a base, and/or, if desired, converting a compound of the formula V or a tautomer thereof, in each case in free form or in salt form, which can be obtained according to the process or by a different method, into a different compound of the formula V or a tautomer thereof, separating an isomer mixture which can be obtained according to the process and isolating the desired isomer, and/or converting a free compound of the formula V or a tautomer thereof, which can be obtained according to the process or by a different method, into a salt, or converting a salt of a compound of the formula V or of a tautomer thereof, which can be obtained according to the process or by a different method, into the free compound of the formula V or into a tautomer thereof, or into a different salt.

Variant d):

The reactants can be reacted with each other as such, i.e. without adding a solvent or diluent, for example in the molten state. However, in most eases it is advantageous to add an inert solvent or diluent or a mixture of these. Suitable solvents or diluents are, for example, of the type given under variant b).

The reaction is advantageously carried out in a temperature range from approximately −20° C. to approximately +180° C., preferably from approximately +10° C. to approximately +100° C., in many cases in the range between room temperature and the reflux temperature of the reaction mixture.

In a preferred embodiment of process variant d), the compound V which is obtained is not isolated, but is reacted further in situ, in accordance with the procedure of process variant c), to give a compound II, which in turn can be isolated or again not be isolated, but reacted further in situ, in accordance with the procedure of process variant a), to give a compound I.

Variant e):

Suitable leaving groups X in the compounds VIII are, for example, of the type given in variant b).

Suitable bases for facilitating the detachment of HX are, for example, of the type given in variant b).

The reactants can be reacted with each other as such, i.e. without adding a solvent or diluent, for example in the molten state. However, in most cases it is advantageous to add an inert solvent or diluent or a mixture of these. Suitable solvents or diluents are, for example, of the type given under variant b).

The reaction is advantageously carried out in a temperature range from approximately −20° C. to approximately +180° C., preferably from approximately +10° C. to approximately +100° C., in many cases in the range between room temperature and the reflux temperature of the reaction mixture.

A compound I, II or V which can be obtained according to the process or by a different method can be convened into a different compound I, II or V in a manner known per se by replacing one or more substituents of the starting compound I, II or V in the customary manner by (a) different substituent (s) according to the invention.

Thus, it is possible, for example, to convert compounds I, in which —Z—R$_4$ is —N═C (R$_{15}$)—R$_4$, into compounds I, in which —Z—R$_4$ is —N(H)—C(H)(R$_{15}$)—R$_4$, to convert compounds I or II, in which R$_{16}$ is hydrogen, into compounds I or II, in which R$_{16}$ is other than hydrogen, to convert compounds I, II or V, in which R$_3$ is hydrogen, into compounds I, II or V, in which R$_3$ is other than hydrogen, and to convert compounds I, II or V, in which Y is O, into compounds I, II or V, in which Y is other than O.

Depending on which reaction conditions and starting materials are selected as being suitable for this purpose, it is possible to replace, in one reaction step, only one substituent by a different substituent according to the invention, or several substituents can be replaced in the same reaction step by other substituents according to the invention.

Salts of compounds I, II and V can be prepared in a manner known per se. For example, acid addition salts of compounds I, II and V are obtained by treating them with a suitable acid or a suitable ion-exchanger reagent, and salts with bases an obtained by treating them with a suitable base or a suitable ion-exchanger reagent.

Salts of compounds I, II and V can be converted in the customary manner into the free compounds I, II and V, for example acid addition salts by being treated with a suitable basic agent or a suitable ion-exchanger reagent, and salts with bases, for example, by being treated with a suitable acid or a suitable ion-exchanger reagent.

Salts of compounds I, II and V can be converted in a manner known per se into different salts of compounds I, II and V, for example acid addition salts into different acid addition salts, for example by treating a salt of an inorganic acid, such as a hydrochloride, with a suitable metal salt, such as a sodium salt, barium salt or silver salt, of an acid, for example using silver acetate, in a suitable solvent, in which an inorganic salt which is being formed, for example silver chloride, is insoluble and so separates out from the reaction mixture.

Depending on the procedure and the reaction conditions, the compounds I, II and V which have salt-forming properties can be obtained in free form or in the form of salts.

The compounds I, II and V and in each case, if appropriate, the tautomer thereof, in each case in free form or in salt form, can be present in the form of one of the isomers which are possible or as a mixture of these, for example as pure isomers, such as antipodes and/or diastereomers, or as isomer mixtures, such as enantiomer mixtures, for example racemates, diastereomer mixtures or racemate mixtures, depending on the number and the absolute and relative configuration of asymmetric carbon atoms in the molecule and/or depending on the configuration of non-aromatic double bonds in the molecule; the invention relates to the pure isomers and to all isomer mixtures which are possible and is to be understood accordingly in each case hereinabove and hereinafter, even when stereochemical details are not mentioned specifically in each individual case.

Diastereomer mixtures and racemate mixtures of compounds I, II or V, in free form or in salt form, which can be obtained according to the process—depending on which starting materials and procedures are selected—or by other routes, can be separated on the basis of the physicochemical differences of the components in the known manner to give the pure diastereomers or racemates, for example by fractional crystallisation, distillation and/or chromatography.

Enantiomer mixtures which can be obtained accordingly, such as racemates, can be resolved by known methods to give the optical antipodes, for example by recrystallisation from an optically active solvent, by chromatography on chiral adsorbents, for example high-pressure liquid chromatography (HPLC) on acetylcellulose, with the aid of suitable microorganisms, by cleavage using specific, immobilised enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric acid, tartaric acid or malic acid, or a sulfonic acid, for example camphoric sulfonic acid, and separating the resulting mixture of diastereomers, for example by fractional crystallisation since they differ with regard to their solubility properties, to give the diastereomers, from which the enantiomer desired can be liberated by allowing suitable agents, for example bases, to act on them.

Pure diastereomers or enantiomers can be obtained according to the invention not only by separating suitable isomer mixtures but also by generally known methods of diastereoselective or enantioselective synthesis, for example by carrying out the process according to the invention using stereochemically suitable educts.

If the individual components differ with regard to their biological activity, it is advantageous to isolate, or synthesis, in each case the biologically more effective isomer, for example enantiomer or diastereomer, or isomer mixture, for example enantiomer mixture or diastereomer mixture.

The compounds I, II and V, in free form or in salt form, can also be obtained in the form of their hydrates and/or can also include other solvents, for example solvents which may be used for crystallising compounds in solid form.

The invention relates to all those embodiments of the process in which, starting from a starting material or intermediate which can be obtained in any desired step of the process, all or some of the missing steps are carried out or a starting material is used in the form of a derivative or salt thereof and/or the racemates or antipodes thereof or, in particular, formed under the reaction conditions.

Starting materials and intermediates, in each case in free form or in salt form, which are used in the process of the present invention are preferably those which lead to the compounds I which have been described at the outset as being particularly valuable, or to salts thereof.

The invention particularly relates to the preparation processes described in Examples H1 to H16.

The invention furthermore relates to starting materials and intermediates, in each case in free form or in salt form, which are novel and which are used according to the invention for the preparation of the compounds I or salts thereof, to a process for their preparation and to their use as starting materials and intermediates for the preparation of the compounds I; in particular, this applies to the compounds I, II and V.

The compounds I according to the invention are valuable as preventive and/or curative active ingredients in the field of pest control, even at low rates of application, and have a highly favourable biocidal spectrum while being well tolerated by warm-blooded species, fish and plants. The active ingredients according to the invention are active against all or individual development stages of normally sensitive, but also resistant, animal pests, such as insects or representatives of the order Acarina. The insecticidal or acaricidal activity of the active ingredients according to the invention can in this case become apparent either directly, i.e. from a destruction of the pest which occurs either immediately or only after some time has elapsed, for example during moulting, or indirectly, for example from reduced oviposition and/or hatching rates, the good activity corresponding to a mortality rate of not less than 50 to 60%.

The abovementioned animal pests include, for example: from the order Lepidoptera, for example, Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cantella, Carposina nipponensis, Chilo spp., Choristoneura spp., Clysia ambiguella, Cnaphalocrocis spp., Cnephasia spp., Cochylis spp., Coleophora spp., Crocidolomia binomlis, Cryptophiebia leucotrem, Cydia spp., Diawaea spp., Diparopsis castanea, Earlas spp., Ephestia spp., Eucosma spp., Eupoecilia ambiguella, Euprocris spp., Euxoa spp., Grapholita spp., Hedya nubiferana, Heliotis spp., Hellula undalis, Hyphanuia cunea, Keifefta lycopersicella, Leucoptera scitella, Lithocollethis spp., Lobesia botrana, Lymantria spp., Lyonetia spp., Malacosoma spp., Mamestra brassicae, Manduca sexta, Operophtera spp., Ostrinia nubilalis, Pammene spp., Pandemis spp., Panolis flammea, Pectinophora gossypiella, Phthorimaea opercnlella, Pieris rapae, Pieris spp., Plutella xylosiella, Prays spp., Scirpophaga spp., Sesamia spp., Sparganoflxis spp., Spodopiera spp., Synanthedon spp., Thaumetopoca spp., Tortfix spp., Trichoplusia ni and Yponomeuta spp.;

from the order Coleoptera, for example,

Agriotes spp., Anthonomus spp., Atomaria lincaris, Chactocnema tibialis, Cosmopoliies spp., Curculio spp., Dermcsies spp., Diabrotica spp., Epilachna spp., Eremnus spp., Leptinotarsa decemlineata, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example,

Blatla spp., Blattella spp., Gryllotalpa spp., Leucophaea maderae, Locusta spp., Periplaneta spp. and Schistocerca spp.;

from the order Isoptera, for example,

Reticulitermes spp.;

from the order Psocoptera, for example,

Liposcelis spp.;

from the order Anoplura, for example,

Haematopinus spp., Linognathus spp., Pediculus spp., Pemphigus spp. and Phylloxera spp.;

from the order Mallophaga, for example,

Damalinea spp. and Trichodectes spp.;

from the order Thysanoptera, for example,

Frankliniella spp., Hercinothrips spp., Taeniothrips spp., Thrips palmi, Thrips tabaci and Scirotluips aurantii;

from the order Heteroptera, for example,

Cimex spp., Distantiella theobroma, Dysdercus spp., Euchistus spp. Eurygaster spp. Leptocorisa spp., Nezara spp., Piesma spp., Rhodnius spp., Sahlbergella singularis, Scotinophara spp. and Triatoma spp.;

from the order Homoptera, for example,

Aleurothrixus fioccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepiclosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidioms spp., Rhopalosiphum spp., Saissetia spp., Scaphoideus spp., Schizaphis spp., Sitobion spp., Trialeurodes vaporariorum, Trioza erytreaeand Unaspis citri;

from the order Hymenoptera, for example,

Acromyrmex, Atta spp., Cephus spp., Diprion spp., Diprionidae, Gilpinia polytoma, Hoplocampa spp., Lasius spp., Monomorium phanonis, Neodiprion spp., Solenopsis spp. and Vespa spp.;

from the order Diptera, for example,

Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp.and Tipula spp.;

from the order Siphonaptera, for example,

Ceratophyllus spp. and Xenopsylla cheopis;

from the order Thysanura, for example,

Lepisma saccharina and from the order Acarina, for example,

Acarus siro, Aceria sbeldoni, Aculus schlechtendali, Amblyomma spp., Argas spp., Boophilus spp., Brevipalpus spp., Bryobia praetiosa, Calipitrimenus spp., Chorioptes spp., Dermanyssus gallinae, Eotetranychus carpini, Eriophyes spp., Hyalomma spp., Ixodes spp., Olygonychus pratensis, Ornithodoros spp., Panonychus spp., Phyllocoptruta oleivora, Polyphagotarsonemus latus, Psoroptes spp., Rhipicephalus spp., Rhizogiyphus spp., Sarcoptes spp., Tarsonemus spp. and Tetranychus spp.

The active ingredients according to the invention allow pests of the abovementioned type which can be found, in particular, on plants, especially useful plants and oronmentals in agriculture, horticulture and silviculture, or on parts of such plants, such as fruits, flowers, foliage, stalks, tubers or roots, to be controlled, i.e. contained or destroyed, and in some cases the protection against the pests extends to parts which are formed at a later point in time.

Target crops which are possible are, in particular, cereals, such as wheat, barley, rye, oats, rice, maize or sorghum; beet, such as sugar beet or fodder beet; fruit, for example pomaceous fruit, stone fruit and soft fruit, such as apples, pears, plums, peaches, almonds, cherries or berries, for example strawberries, raspberries or blackberries; legnminous plants, such as beans, lentils, peas or soya beans; oil crops, such as oilseed rape, mustard, poppies, olives, sunflowers, coconuts, castor, cocoa or groundnuts; cucurbits, such as pumpkins, cucumbers or melons; fibre plants, such as cotton, flax, hemp or jute; citrous fruits, such as oranges, lemons, grapefruit or tangerines; vegetables, such as spinach, lettuce, asparagus, cabbages, carrots, onions, tomatoes, potatoes or bell peppers; species from the laurel family, such as avocado, cinnamon or camphor, and tobacco, nuts, coffee, egg plants, sugar cane, tea, pepper, grapes, hops, species from the banana family, latex plants and ornamentals.

The active ingredients according to the invention are particularly suitable for controlling *Aphis craccivora, Bemisia tabaci, Myzus persicae, Nephotettix cincticeps* and *Nilaparvata lugens* in vegetable, fruit and rice crops.

Other fields of application for the active ingredients according to the invention are the protection of stored products and stores and of material and, in the hygiene sector, in particular the protection of domestic animals and productive livestock against pests of the abovementioned type.

The invention therefore also relates to pesticidal compositions, such as emulsifiable concentrates, suspension concentrates, directly sprayable or dilutable solutions, spreadable pastes, dilute emulsions, wettable powders, soluble powders, dispersible powders, dusts, granules or encapsulations in polymeric substances, all of which comprise at least one of the active ingredients according to the invention and are to be selected depending on the intended aims and the prevailing circumstances.

In these compositions, the active ingredient is used as a pure active ingredient, for example a solid active ingredient in a specific particle size or, preferably, together with at least one of the auxiliaries conventionally used in the an of formulation, such as extenders, for example solvents or solid carriers, or such as surface-active compounds (surfactants).

The following are examples of suitable solvents: partially hydrogenated or unhydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and their ethers and esters, such as propylene glycol, dipropylene glycol ether, ethylene glycol, ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, or water, epoxidized and unepoxidized vegetable oils, such as epoxidized and unoxidized rapeseed oil, castor oil, coconut oil or soya oil, and silicone oils.

Solid carriers which are used, for example for dusts and dispersible powders, are, as a rule, ground natural minerals, such as calcite, talc, kaolin, montmorillonite or attapulgite. To improve the physical properties, it is also possible to add highly-disperse silicas or highly-disperse absorptive polymers. Possible particulate, adsorptive carriers for granules are either porous types, for example pummice, brick grit, sepiolite or bentonite, or non-sorptive carrier materials, for example calcite or sand. Moreover, a large number of granulated materials of inorganic or organic nature can be used, in particular dolomite or comminuted plant residues.

Suitable surface-active compounds are non-ionic, cationic and/or anionic surfactants or surfactant mixtures which have good emulsifying, dispersing and wetting properties, depending on the nature of the active ingredient to be formulated. The surfactants listed hereinbelow are in this case only to be regarded as examples; a large number of other surfactants conventionally used in the an of formulation and suitable according to the invention are described in the specialist literature.

Suitable non-ionic surfactants are mainly polyglycol ether derivatives of aliphatic or cycloaliphatic alcohols, saturated or unsaturated fatty acids and alkylphenols, which can have 3 to 30 glycol ether groups and 8 to 20 carbon atoms in the (aliphatic) hydrocarbon radical and 6 to 18 carbon atoms in the alkyl radical of the alkylphenols. Other suitable non-ionic surfactants are water-soluble polyethylene oxide adducts with polypropylene glycol, ethylene diaminopolypropylene glycol and alkyl polypropylene glycol which have 1 to 10 carbon atoms in the alkyl chain and 20 to 250 ethylene glycol ether groups and 10 to 100 propylene glycol ether groups. The abovementioned compounds customarily have 1 to 5 ethylene glycol units per propylene glycol unit. Examples which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Other substances which are suitable are fatty acid esters of polyoxyethylene sorbitan, such as polyoxyethylene sorbitan trioleate.

The cationic surfactants are mainly quaternary ammonium salts which have, as substituents, at least one alkyl radical having 8 to 22 C atoms and, as further substituents, lower, halogenated or unhalogenated alkyl, benzyl or lower hydroxyalkyl radicals. The salts are preferably in the form of halides, methylsulfates or ethylsulfates. Examples are stearyltrimethylammonium chloride and benzyldi(2-chloroethyl)ethylammonium bromide.

Suitable artionic surfactants can be either water-soluble soaps or water-soluble, synthetic surface-active compounds. Soaps which are suitable are the alkali metal salts, alkaline earth metal salts and substituted or unsubstituted ammonium salts of higher fatty acids ($C_{10}$–$C_{22}$), such as the sodium salts or potassium salts of oleic or stearic acid, or of natural mixtures of fatty acids which can be obtained, for example, from coconut oil or tall oil; the fatty acid methyltaurates must also be mentioned. However, synthetic surfactants are used more frequently, in particular fatty sulfonates, fatty sulfates, sulfonated benzimidazole derivatives or alkylarylsulfonates. The fatty sulfonates and fatty sulfates are, as a rule, in the form of alkali metal salts, alkaline earth metal salts or substituted or unsubstituted ammonium salts and have, as a rule, an alkyl radical having 8 to 22 C atoms, alkyl also including the alkyl moiety of acyl radicals, for example the sodium salt or the calcium salt of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives have preferably 2 sulfonyl groups and one fatty acid radical having approximately 8 to 22 C atoms. Alkylarylsulfonates are, for example, the sodium salts, calcium salts or triethanolammonium salts of dodecylbenzenesulfonic acid, of dibutylnaphthalenesulfonic acid or of a naphthalenesulfonic acid/formaldehyde condensation product. Suitable phosphates, such as salts of the phosphoric ester of a p-nonylphenol-(4–14)ethylene oxide adduct, or phospholipids, are also suitable.

As a rule, the compositions comprise 0.1 to 99%, in particular 0.1 to 95%, of active ingredient and 1 to 99.9%, in particular 5 to 99.9%, of—at least—one solid or liquid auxiliary, it being possible, as a rule, for 0 to 25%, in particular 0.1 to 20%, of the composition to be surfactants (% in each case meaning per cent by weight). While concentrated compositions are more preferred as commercially available goods, the end consumer uses, as a rule, dilute compositions with considerably lower concentrations of active ingredients. Preferred compositions are, in particular, composed as follows (%=per cent by weight):

Emulsifiable concentrates:

| Emulsifiable concentrates: | |
| --- | --- |
| Active ingredient: | 1 to 90%, preferably 5 to 20% |
| Surfactant: | 1 to 30%, preferably 10 to 20% |
| Solvent: | 5 to 98%, preferably 70 to 85% |
| Dusts: | |
| Active ingredient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surfactant: | 1 to 40%, preferably 2 to 30% |
| Wettable powders: | |
| Active ingredient: | 0.5 to 90%, preferably 1 to 80% |
| Surfactant: | 0.5 to 20%, preferably 1 to 15% |
| Solid carrier: | 5 to 99%, preferably 15 to 98% |
| Granules: | |
| Active ingredient: | 0.5 to 30%, preferably 3 to 15% |
| Solid carrier: | 99.5 to 70%, preferably 97 to 85% |

The activity of the compositions according to the invention can be broadened considerably and adapted to prevailing circumstances by adding other insecticidal active ingredients. Representatives of the following active ingredient classes are examples of suitable additions of active ingredients: organophosphorus compounds, nitrophenols and derivatives, formamidines, acrylureas, carbamates, pyrethroids, nitroenamines and derivatives, pyrrols, thioureas and derivatives, chlorinated hydrocarbons and *Bacillus thuringiensis* preparations. The compositions according to the invention can also comprise other solid or liquid auxiliaries, such as stabilizers, for example epoxidized or unepoxidized vegetable oils (for example epoxidized coconut oil, rapeseed oil or soya oil), antifoams, for example silicone oil, preservatives, viscosity regulators, binders and/ or tackifiers, and also fertilizers and other active ingredients for achieving specific effects, for example acaricides, bactericides, fungicides, nematocides, molluscicides or selective herbicides.

The compositions according to the invention are prepared in a known manner, in the absence of auxiliaries, for example by grinding, screening and/or compressing a solid active ingredient or active ingredient mixture, for example to give a certain particle size, and in the presence of at least one auxiliary, for example, by intimately mixing and/or grinding the active ingredient or active ingredient mixture with the auxiliary or auxiliaries. The invention also provides these processes for the preparation of the compositions according to the invention and the use of the compounds I for the preparation of these compositions.

The invention also provides the methods of application for the composition, i.e. the methods for controlling pests of the abovementioned type, such as spraying, atomizing, dusting, brushing on, seed-dressing, scattering or pouring, depending on the intended aims and the prevailing circumstances, and the use of the compositions for controlling pests of the abovementioned type. Typical rates of application are between 0.1 and 1,000 ppm, preferably between 0.1 and 500 ppm, of active ingredient. The rates of application per hectare are, as a rule, 1 to 2,000 g of active ingredient per hectare, in particular 10 to 1,000 g/ha, preferably 20 to 600 g/ha.

A preferred method of application in the field of crop protection is application to the foliage of the (plant foliar application), where frequency and rate of application will depend on the risk of infestation with the pest in question. However, the active ingredient can also reach the plants via the root system (systemic action) by drenching the locus of the plants with a liquid composition or incorporating the active ingredient into the locus of the plants, for example into the soil, in solid form, for example in the form of granules (soil application). In paddy rice, such granules can be metered into the flooded paddy field.

The compositions according to the invention are also suitable for protecting plant propagation material, for example seed, such as fruits, tubers or kernels, or plant cuttings, against animal pests. The propagation material can in this case be treated with the composition before planting, for example seed can be dressed before sowing. The active ingredients according to the invention can also be applied to seed kernels (coating), either by soaking the kernels in a liquid composition or by applying a layer of solid composition. The composition can also be applied to the site of application when the propagation material is planted, for example when it is sown into the seed furrow. The invention also provides these treatment methods for plant propagation material and the plant propagation material which has been treated in this manner.

The Examples which follow are not limiting, but only intended to illustrate the invention. Temperatures are given in degrees celsius.

PREPARATION EXAMPLES

Example H 1: 2,3-Dihydro-2-oxo-3-tert-butylcarbonylmethyl-5-trifluoromethyl-1,3,4-oxadiazole.

15 g of Nail dispersed in oil (80%) are washed with petroleum ether until free from oil and treated with 125 ml of N,N-dimethylformamide. A mixture of 77 g of 2,3-dihydro-2-oxo-5-trifluoromethyl-1,3,4-oxadiazole and 250 ml of N,N-dimethylformamide is added dropwise to this suspension in the course of an hour at room temperature. The reaction mixture is stirred for 3 hours, 72.5 g of chloromethyl tert-butyl ketone are added, and the mixture is stirred for a further 16 hours at room temperature and then evaporated. The residue is treated with 1 l of water, and the product which has precipitated is filtered off with suction and dried. This gives the title compound in the form of colourless crystals which melt at 69°–71°.

Example H2: 1-Acetylamino-2,3-dihydro-3,4-dimethyl-2-oxo-1H-imidazole (compound no. 1.5 in table 1).

68.5 ml of aqueous methylamine solution (40%) are added dropwise to a solution of 78 g of 3-acetylmethyl-2,3-dihydro-5-methyl-2-oxo-1,3,4-oxadiazole in 500 ml of acetonitrile. After the slightly endothermal reaction has subsided, the orange mixture is stirred-for 30 minutes at 48° and then evaporated. The residue is treated with 100 ml of tetrahydrofuran and 200 ml of ethyl acetate, during which process crystals precipitate. The crystals are filtered off, washed with ethyl acetate and dried under reduced pressure at 60°. This gives a mixture of 1-acetylamino-2,3-dihydro-3,4-dimethyl-2-oxo-1H-imidazole and 1-acetylamino-3,4-dimethyl-4-methylamino-2-oxo-imidazolidine. A sample of this mixture is separated on silica gel using ethyl acetate/methanol (2:1) as eluent, yielding the pure 1-acetylamino-2,3-dihydro-3,4-dimethyl-2-oxo-1H-imidazole which melts at 199°–201° and the pure 1-acetylamino-3,4-dimethyl-4-methylamino-2-oxo-imidazolidine which melts with decomposition at 150°–152°. Another sample of the above-mentioned mixture is heated to 175° and held at this temperature until the evolution of methylamine gas has ceased. The residue is cooled and stirred with a small amount of methanol. Filtration of the suspension gives the pure title compound melting after drying at 199°–201°.

Example H3

Analogously to the procedure described in Example H2 also the other compounds listed in table 1 can be prepared. The temperatures given in the column "Physical Data" of this table in each case denote the melting point of the compound in question.

TABLE 1

$$R_3 \underset{N}{\overset{R_1}{\diagdown}} \underset{O}{\diagdown} \overset{N}{\diagdown} N(H)C(=O)Q$$

| Compound No. | $R_1$ | $R_3$ | Q | Physical Data |
|---|---|---|---|---|
| 1.1 | $C_4H_9(t)$ | H | $CF_3$ | |
| 1.2 | $C_3H_7(i)$ | $CH_3$ | $CH_3$ | |
| 1.3 | $CH_3$ | H | $CH_3$ | 164–166° |
| 1.4 | $C_3H_5(cyclo)$ | $C_3H_7(i)$ | $CF_3$ | |
| 1.5 | $CH_3$ | $CH_3$ | $CH_3$ | 199–201° |
| 1.6 | $CH_3$ | $C_2H_5$ | $CH_3$ | 204–206° |
| 1.7 | $C_4H_9(t)$ | H | $CH_3$ | |
| 1.8 | $C_3H_5(cyclo)$ | $C_3H_7(i)$ | $CH_3$ | |
| 1.9 | $CH_3$ | H | $C_2H_5$ | |
| 1.10 | $C_3H_5(cyclo)$ | $C_3H_7(i)$ | $C_2H_5$ | |
| 1.11 | $CH_3$ | $CH_3$ | $C_2H_5$ | |
| 1.12 | $CH_3$ | $C_2H_5$ | $C_2H_5$ | |
| 1.13 | $C_4H_9(t)$ | H | $C_2H_5$ | |

Example H4: 1-Amino-2,3-dihydro-3,4-dimethyl-2-oxo-1H-imidazole hydrochloride (compound no. 4.2A.1 in table 2).

0.8 g of 1-acetylamino-2,3-dihydro-3,4-dimethyl-2-oxo-1H-imidazole are suspended in 800 ml of methanol, and the suspension is then heated to 42°. At this temperature, 28 g of gaseous HCl are passed into the suspension in the course of 40 minutes, during which process the suspension turns into a solution and the temperature of the reaction mixture rises to 52°. The solution is concentrated on a rotary evaporator, the residue is stirred with a small amount of tetrahydrofuran, and the crystals which have precipitated are filtered off with suction and dried, yielding the title salt melting at 162°–165°.

Example H5: 1-Amino-2,3-dihydro-3-methyl-2-oxo-4-tert-butyl-1H-imidazole (compound no. 9.2A in table 2).

75 ml of aqueous methylamine solution (40%) are added to a solution of 12.6 g of 2,3-dihydro-2-oxo-3-tert-butylcarbonylmethyl-5-trifluoromethyl-1,3,4-oxadiazole in 50 ml of acetonitrile. After the slightly exothermal reaction has subsided, the reaction mixture is stirred for 2 hours at room temperature and then for 14 hours at 80° and then evaporated the liquid residue is treated with ice-water, and the aqueous mixture is extracted three times by shaking with ethyl acetate. The combined ethyl acetate phases are dried and evaporated, and the oily orange residue is recrystallized from hexane. This gives the title compound in the form of pale yellow crystals which melt at 100°–105°.

Example H6: 1-Amino-2,3-dihydro-2-oxo4-tert-butyl-1H-imidazole (compound no. 9.1A in table 2)

75 ml of aqueous ammonia solution (25%) are added to a solution of 25.6 g of 2,3-dihydro-2-oxo-3-tert-butylcarbonylmethyl-5-trifluoromethyl-1,3,4-oxadiazole in 100 ml of acetonitrile. After the slightly exothermal reaction has subsided, the reaction mixture is stirred for 2 hours at room temperature and then for 14 hours at 80° and then evaporated, the residue is treated with trichloromethane, and the trichloromethane mixture is freed from the undissolved components, dried and evaporated. The residue is triturated with diethyl ether and subjected to filtration with suction. This gives the title compound in the form of pale yellow crystals which melt at 197–200°.

Example H7

Analogously to the procedures described in Examples H4 to H6 also the other compounds listed in table 2 can be prepared. The temperatures given in the column "Physical Data" of this table in each case denote the melting point of the compound in question.

TABLE 2

$$\begin{array}{c} R_1 \quad R_2 \\ \diagdown \diagup \\ N \quad N \\ R_3 \diagdown \diagup \diagdown NH_2 \\ \| \\ O \end{array}$$

| Compound No. | $R_2$ | $R_3$ | $R_1$ | Physical Data |
|---|---|---|---|---|
| 3.1A | H | H | H | |
| 3.2A | H | $CH_3$ | H | |
| 3.3A | H | $C_2H_5$ | H | |
| 3.4A | H | $C_3H_5$(cyclo) | H | |
| 3.5A | H | $C_3H_7$(n) | H | |
| 3.6A | H | $C_3H_7$(i) | H | |
| 3.7A | H | $C_4H_9$(n) | H | |
| 3.8A | H | $C_4H_9$(t) | H | |
| 3.9A | H | $CH_2CH=CH_2$ | H | |
| 3.10A | H | $CH_2C(CH_3)=CH_2$ | H | |
| 3.11A | H | $CH_2C(Br)=CH_2$ | H | |
| 3.12A | H | $CH_2C\equiv CH$ | H | |
| 3.13A | H | $CH_2C(=O)CH_3$ | H | |
| 3.14A | H | $CH_2C(=O)C_2H_5$ | H | |
| 3.15A | H | $C(=O)CH_3$ | H | |
| 3.16A | H | $C(=O)C_2H_5$ | H | |
| 3.17A | H | $C(=O)C_3H_7$(i) | H | |
| 3.18A | H | $C(=O)OC_2H_5$ | H | |
| 3.19A | H | $C(=O)OC_2H_5$ | H | |
| 3.20A | H | $C(=O)N(CH_3)_2$ | H | |
| 3.21A | H | $C(=O)N(OCH_3)CH_3$ | H | |
| 3.22A | H | $CH_2CH(OCH_3)_2$ | H | |
| 3.23A | H | $CH_2CH(OC_2H_5)_2$ | H | |
| 3.24A | H | $CH_2CH_2OCH_3$ | H | |
| 3.25A | H | $CH_2CN$ | H | |
| 3.26A | H | $CH_2C(=O)OC_2H_5$ | H | |
| 3.27A | H | $CH_2CH_2C(=O)OC_2H_5$ | H | |
| 3.28A | H | $(CH_2)_3C(=O)OC_2H_5$ | H | |
| 3.29A | H | $(CH_2)_4C(=O)OC_2H_5$ | H | |
| 3.30A | H | $N=C$(pyrid-3-yl)H | H | |
| 3.31A | H | $N=C(C_6H_5)H$ | H | |
| 3.32A | H | $CH_2OCH_3$ | H | |
| 3.33A | H | $CH_2OC_2H_5$ | H | |
| 3.34A | H | $CH_2CH_2OC_2H_5$ | H | |
| 3.35A | H | $CH_2CH_2Cl$ | H | |
| 3.36A | H | $CHF_2$ | H | |
| 3.37A | H | $CF_2CHF_2$ | H | |
| 3.38A | H | $CH_2SCH_3$ | H | |
| 3.39A | $CH_3$ | H | H | |
| 3.40A | $CH_3$ | $CH_3$ | H | |
| 3.41A | $CH_2CH=CH_2$ | $CH_2CH=CH_2$ | H | |
| 3.42A | $CH_2C(Br)=CH_2$ | $CH_2C(Br)=CH_2$ | H | |
| 3.43A | H | $C(=O)CH_2OCH_3$ | H | |
| 3.44A | H | $C(=O)CH_2CH_2CH_3$ | H | |
| 3.45A | $CH_3$ | $C(=O)CH_2OCH_3$ | H | |
| 3.46A | $CH_3$ | $C(=O)CH(CH_3)_2$ | H | |
| 3.47A | $CH_3$ | $C_2H_5$ | H | |
| 3.48A | $CH_3$ | $C_3H_5$(cyclo) | H | |
| 3.49A | $CH_3$ | $C_3H_7$(n) | H | |
| 3.50A | $CH_3$ | $C_4H_9$(n) | H | |
| 4.1A | H | H | $CH_3$ | 195–198° |
| 4.2A | H | $CH_3$ | $CH_3$ | |
| 4.2A.1 | Hydrochloride of compound no. 4.2A | | | 162–165° |
| 4.3A | H | $C_2H_5$ | $CH_3$ | |
| 4.3A.1 | Hydrochloride of compound no. 4.3A | | | 147° |
| 4.4A | H | $C_3H_5$(cyclo) | $CH_3$ | |
| 4.5A | H | $C_3H_7$(n) | $CH_3$ | |
| 4.6A | H | $C_3H_7$(i) | $CH_3$ | |
| 4.7A | H | $C_4H_9$(n) | $CH_3$ | |
| 4.8A | H | $C_4H_9$(t) | $CH_3$ | |
| 4.9A | H | $CH_2CH=CH_2$ | $CH_3$ | |
| 4.10A | H | $CH_2C(CH_3)=CH_2$ | $CH_3$ | |
| 4.11A | H | $CH_2C(Br)=CH_2$ | $CH_3$ | |
| 4.12A | H | $CH_2C\equiv CH$ | $CH_3$ | |
| 4.13A | H | $CH_2C(=O)CH_3$ | $CH_3$ | |
| 4.14A | H | $CH_2C(=O)C_2H_5$ | $CH_3$ | |
| 4.15A | H | $C(=O)CH_3$ | $CH_3$ | |
| 4.16A | H | $C(=O)C_2H_5$ | $CH_3$ | |

TABLE 2-continued $$\underset{R_3}{\overset{R_1}{\underset{N}{\bigvee}}}\underset{\overset{\parallel}{O}}{\overset{}{N}}\underset{NH_2}{\overset{R_2}{\bigvee}}$$

| Compound No. | $R_2$ | $R_3$ | $R_1$ | Physical Data |
|---|---|---|---|---|
| 4.17A | H | C(=O)C$_3$H$_7$(i) | CH$_3$ | |
| 4.18A | H | C(=O)OCH$_3$ | CH$_3$ | |
| 4.19A | H | C(=O)OC$_2$H$_5$ | CH$_3$ | |
| 4.20A | H | C(=O)N(CH$_3$)$_2$ | CH$_3$ | |
| 4.21A | H | C(=O)N(OCH$_3$)CH$_3$ | CH$_3$ | |
| 4.22A | H | CH$_2$CH(OCH$_3$)$_2$ | CH$_3$ | |
| 4.23A | H | CH$_2$CH(OC$_2$H$_5$)$_2$ | CH$_3$ | |
| 4.24A | H | CH$_2$CH$_2$OCH$_3$ | CH$_3$ | |
| 4.25A | H | CH$_2$CN | CH$_3$ | |
| 4.26A | H | CH$_2$C(=O)OC$_2$H$_5$ | CH$_3$ | |
| 4.27A | H | CH$_2$CH$_2$C(=O)OC$_2$H$_5$ | CH$_3$ | |
| 4.28A | H | (CH$_2$)$_3$C(=O)OC$_2$H$_5$ | CH$_3$ | |
| 4.29A | H | (CH$_2$)$_4$C(=O)OC$_2$H$_5$ | CH$_3$ | |
| 4.30A | H | N-C(pyrid-3-yl)H | CH$_3$ | |
| 4.31A | H | N=C(C$_6$H$_5$)H | CH$_3$ | |
| 4.32A | H | CH$_2$OCH$_3$ | CH$_3$ | |
| 4.33A | H | CH$_2$OC$_2$H$_5$ | CH$_3$ | |
| 4.34A | H | CH$_2$CH$_2$OC$_2$H$_5$ | CH$_3$ | |
| 4.35A | H | CH$_2$CH$_2$Cl | CH$_3$ | |
| 4.36A | H | CHF$_2$ | CH$_3$ | |
| 4.37A | H | CF$_2$CHF$_2$ | CH$_3$ | |
| 4.38A | H | CH$_2$SCH$_3$ | CH$_3$ | |
| 4.39A | CH$_3$ | H | CH$_3$ | |
| 4.40A | CH$_3$ | CH$_3$ | CH$_3$ | |
| 4.41A | CH$_2$CH=CH$_2$ | CH$_2$CH=CH$_2$ | CH$_3$ | |
| 4.42A | CH$_2$C(Br)=CH$_2$ | CH$_2$C(Br)=CH$_2$ | CH$_3$ | |
| 4.43A | H | C(=O)CH$_2$OCH$_3$ | CH$_3$ | |
| 4.44A | H | C(=O)CH$_2$CH$_2$CH$_3$ | CH$_3$ | |
| 4.45A | CH$_3$ | C(=O)CH$_2$OCH$_3$ | CH$_3$ | |
| 4.46A | CH$_3$ | C(=O)CH(CH$_3$)$_2$ | CH$_3$ | |
| 5.1A | H | H | C$_2$H$_5$ | |
| 5.2A | H | CH$_3$ | C$_2$H$_5$ | |
| 5.3A | H | C$_2$H$_5$ | C$_2$H$_5$ | |
| 5.4A | H | C$_3$H$_5$(cyclo) | C$_2$H$_5$ | |
| 5.5A | H | C$_3$H$_7$(n) | C$_2$H$_5$ | |
| 5.6A | H | C$_3$H$_7$(i) | C$_2$H$_5$ | |
| 5.7A | H | C$_4$H$_9$(n) | C$_2$H$_5$ | 183–184° |
| 5.8A | H | C$_4$H$_9$(t) | C$_2$H$_5$ | |
| 5.9A | H | CH$_2$CH=CH$_2$ | C$_2$H$_5$ | |
| 5.10A | H | CH$_2$C(CH$_3$)=CH$_2$ | C$_2$H$_5$ | |
| 5.11A | H | CH$_2$C(Br)=CH$_2$ | C$_2$H$_5$ | |
| 5.12A | H | CH$_2$C≡CH | C$_2$H$_5$ | |
| 5.13A | H | CH$_2$C(=O)CH$_3$ | C$_2$H$_5$ | |
| 5.14A | H | CH$_2$C(=O)C$_2$H$_5$ | C$_2$H$_5$ | |
| 5.15A | H | C(=O)CH$_3$ | C$_2$H$_5$ | |
| 5.16A | H | C(=O)C$_2$H$_5$ | C$_2$H$_5$ | |
| 5.17A | H | C(=O)C$_3$H$_7$(i) | C$_2$H$_5$ | |
| 5.18A | H | C(=O)OCH$_3$ | C$_2$H$_5$ | |
| 5.19A | H | C(=O)OC$_2$H$_5$ | C$_2$H$_5$ | |
| 5.20A | H | C(=O)N(CH$_3$)$_2$ | C$_2$H$_5$ | |
| 5.21A | H | C(=O)N(OCH$_3$)CH$_3$ | C$_2$H$_5$ | |
| 5.22A | H | CH$_2$CH(OCH$_3$)$_2$ | C$_2$H$_5$ | |
| 5.23A | H | CH$_2$CH(OC$_2$H$_5$)$_2$ | C$_2$H$_5$ | |
| 5.24A | H | CH$_2$CH$_2$OCH$_3$ | C$_2$H$_5$ | |
| 5.25A | H | CH$_2$CN | C$_2$H$_5$ | |
| 5.26A | H | CH$_2$C(=O)OC$_2$H$_5$ | C$_2$H$_5$ | |
| 5.27A | H | CH$_2$CH$_2$C(=O)OC$_2$H$_5$ | C$_2$H$_5$ | |
| 5.28A | H | (CH$_2$)$_3$C(=O)OC$_2$H$_5$ | C$_2$H$_5$ | |
| 5.29A | H | (CH$_2$)$_4$C(=O)OC$_2$H$_5$ | C$_2$H$_5$ | |
| 5.30A | H | N=C(pyrid-3-yl)H | C$_2$H$_5$ | |
| 5.31A | H | N=C(C$_6$H$_5$)H | C$_2$H$_5$ | |
| 5.32A | H | CH$_2$OCH$_3$ | C$_2$H$_5$ | |
| 5.33A | H | CH$_2$OC$_2$H$_5$ | C$_2$H$_5$ | |
| 5.34A | H | CH$_2$CH$_2$OC$_2$H$_5$ | C$_2$H$_5$ | |
| 5.35A | H | CH$_2$CH$_2$Cl | C$_2$H$_5$ | |
| 5.36A | H | CHF$_2$ | C$_2$H$_5$ | |
| 5.37A | H | CF$_2$CHF$_2$ | C$_2$H$_5$ | |
| 5.38A | H | CH$_2$SCH$_3$ | C$_2$H$_5$ | |
| 5.39A | CH$_3$ | H | C$_2$H$_5$ | |

TABLE 2-continued

[Structure: R1 and R2 on a ring with N-R3 and N-NH2, C=O]

| Compound No. | $R_2$ | $R_3$ | $R_1$ | Physical Data |
|---|---|---|---|---|
| 5.40A | $CH_3$ | $CH_3$ | $C_2H_5$ | |
| 5.41A | $CH_2CH=CH_2$ | $CH_2CH=CH_2$ | $C_2H_5$ | |
| 5.42A | $CH_2C(Br)=CH_2$ | $CH_2C(Br)=CH_2$ | $C_2H_5$ | |
| 5.43A | H | $C(=O)CH_2OCH_3$ | $C_2H_5$ | |
| 5.44A | H | $C(=O)CH_2CH_2CH_3$ | $C_2H_5$ | |
| 5.45A | $CH_3$ | $C(=O)CH_2OCH_3$ | $C_2H_5$ | |
| 5.46A | $CH_3$ | $C(=O)CH(CH_3)_2$ | $C_2H_5$ | |
| 6.1A | H | H | $C_3H_7(n)$ | |
| 6.2A | H | $CH_3$ | $C_3H_7(n)$ | |
| 6.3A | H | $C_2H_5$ | $C_3H_7(n)$ | |
| 6.4A | H | $C_3H_5(cyclo)$ | $C_3H_7(n)$ | |
| 6.5A | H | $C_3H_7(n)$ | $C_3H_7(n)$ | |
| 6.6A | H | $C_3H_7(i)$ | $C_3H_7(n)$ | |
| 6.7A | H | $C_4H_9(n)$ | $C_3H_7(n)$ | |
| 6.8A | H | $C_4H_9(t)$ | $C_3H_7(n)$ | |
| 6.9A | H | $CH_2CH=CH_2$ | $C_3H_7(n)$ | |
| 6.10A | H | $CH_2C(CH_3)=CH_2$ | $C_3H_7(n)$ | |
| 6.11A | H | $CH_2C(Br)=CH_2$ | $C_3H_7(n)$ | |
| 6.12A | H | $CH_2C\equiv CH$ | $C_3H_7(n)$ | |
| 6.13A | H | $CH_2C(=O)CH_3$ | $C_3H_7(n)$ | |
| 6.14A | H | $CH_2C(=O)C_2H_5$ | $C_3H_7(n)$ | |
| 6.15A | H | $C(=O)CH_3$ | $C_3H_7(n)$ | |
| 6.16A | H | $C(=O)C_2H_5$ | $C_3H_7(n)$ | |
| 6.17A | H | $C(=O)C_3H_7(i)$ | $C_3H_7(n)$ | |
| 6.18A | H | $C(=O)OC_2H_5$ | $C_3H_7(n)$ | |
| 6.19A | H | $C(=O)OC_2H_5$ | $C_3H_7(n)$ | |
| 6.20A | H | $C(=O)N(CH_3)_2$ | $C_3H_7(n)$ | |
| 6.21A | H | $C(=O)N(OCH_3)CH_3$ | $C_3H_7(n)$ | |
| 6.22A | H | $CH_2CH(OCH_3)_2$ | $C_3H_7(n)$ | |
| 6.23A | H | $CH_2CH(OC_2H_5)_2$ | $C_3H_7(n)$ | |
| 6.24A | H | $CH_2CH_2OCH_3$ | $C_3H_7(n)$ | |
| 6.25A | H | $CH_2CN$ | $C_3H_7(n)$ | |
| 6.26A | H | $CH_2C(=O)OC_2H_5$ | $C_3H_7(n)$ | |
| 6.27A | H | $CH_2CH_2C(=O)OC_2H_5$ | $C_3H_7(n)$ | |
| 6.28A | H | $(CH_2)_3C(=O)OC_2H_5$ | $C_3H_7(n)$ | |
| 6.29A | H | $(CH_2)_4C(=O)OC_2H_5$ | $C_3H_7(n)$ | |
| 6.30A | H | $N=C(pyrid-3-yl)H$ | $C_3H_7(n)$ | |
| 6.31A | H | $N=C(C_6H_5)H$ | $C_3H_7(n)$ | |
| 6.32A | H | $CH_2OCH_3$ | $C_3H_7(n)$ | |
| 6.33A | H | $CH_2OC_2H_5$ | $C_3H_7(n)$ | |
| 6.34A | H | $CH_2CH_2OC_2H_5$ | $C_3H_7(n)$ | |
| 6.35A | H | $CH_2CH_2Cl$ | $C_3H_7(n)$ | |
| 6.36A | H | $CHF_2$ | $C_3H_7(n)$ | |
| 6.37A | H | $CF_2CHF_2$ | $C_3H_7(n)$ | |
| 6.38A | H | $CH_2SCH_3$ | $C_3H_7(n)$ | |
| 6.39A | $CH_3$ | H | $C_3H_7(n)$ | |
| 6.40A | $CH_3$ | $CH_3$ | $C_3H_7(n)$ | |
| 6.41A | $CH_2CH=CH_2$ | $CH_2CH=CH_2$ | $C_3H_7(n)$ | |
| 6.42A | $CH_2C(Br)=CH_2$ | $CH_2C(Br)=CH_2$ | $C_3H_7(n)$ | |
| 6.43A | H | $C(=O)CH_2OCH_3$ | $C_3H_7(n)$ | |
| 6.44A | H | $C(=O)CH_2CH_2CH_3$ | $C_3H_7(n)$ | |
| 6.45A | $CH_3$ | $C(=O)CH_2OCH_3$ | $C_3H_7(n)$ | |
| 6.46A | $CH_3$ | $C(=O)CH(CH_3)_2$ | $C_3H_7(n)$ | |
| 7.1A | H | H | $C_3H_7(iso)$ | |
| 7.2A | H | $CH_3$ | $C_3H_7(iso)$ | 80–84° |
| 7.3A | H | $C_2H_5$ | $C_3H_7(iso)$ | |
| 7.4A | H | $C_3H_5(cyclo)$ | $C_3H_7(iso)$ | |
| 7.5A | H | $C_3H_7(n)$ | $C_3H_7(iso)$ | |
| 7.6A | H | $C_3H_7(i)$ | $C_3H_7(iso)$ | |
| 7.7A | H | $C_4H_9(n)$ | $C_3H_7(iso)$ | |
| 7.8A | H | $C_4H_9(t)$ | $C_3H_7(iso)$ | |
| 7.9A | H | $CH_2CH=CH_2$ | $C_3H_7(iso)$ | |
| 7.10A | H | $CH_2C(CH_3)=CH_2$ | $C_3H_7(iso)$ | |
| 7.11A | H | $CH_2C(Br)=CH_2$ | $C_3H_7(iso)$ | |
| 7.12A | H | $CH_2C\equiv CH$ | $C_3H_7(iso)$ | |
| 7.13A | H | $CH_2C(=O)CH_3$ | $C_3H_7(iso)$ | |
| 7.14A | H | $CH_2C(=O)C_2H_5$ | $C_3H_7(iso)$ | |
| 7.15A | H | $C(=O)CH_3$ | $C_3H_7(iso)$ | |

TABLE 2-continued

[Structure: R_1 and R_2 on carbons of a double bond, each connected to N; R_3 on one N; other N connected to NH_2; C=O bridges the two N atoms]

| Compound No. | $R_2$ | $R_3$ | $R_1$ | Physical Data |
|---|---|---|---|---|
| 7.16A | H | $C(=O)C_2H_5$ | $C_3H_7(iso)$ | |
| 7.17A | H | $C(=O)C_3H_7(i)$ | $C_3H_7(iso)$ | |
| 7.18A | H | $C(=O)OC_2H_5$ | $C_3H_7(iso)$ | |
| 7.19A | H | $C(=O)OC_2H_5$ | $C_3H_7(iso)$ | |
| 7.20A | H | $C(=O)N(CH_3)_2$ | $C_3H_7(iso)$ | |
| 7.21A | H | $C(=O)N(OCH_3)CH_3$ | $C_3H_7(iso)$ | |
| 7.22A | H | $CH_2CH(OCH_3)_2$ | $C_3H_7(iso)$ | |
| 7.23A | H | $CH_2CH(OC_2H_5)_2$ | $C_3H_7(iso)$ | |
| 7.24A | H | $CH_2CH_2OCH_3$ | $C_3H_7(iso)$ | |
| 7.25A | H | $CH_2CN$ | $C_3H_7(iso)$ | |
| 7.26A | H | $CH_2C(=O)OC_2H_5$ | $C_3H_7(iso)$ | |
| 7.27A | H | $CH_2CH_2C(=O)OC_2H_5$ | $C_3H_7(iso)$ | |
| 7.28A | H | $(CH_2)_3C(=O)OC_2H_5$ | $C_3H_7(iso)$ | |
| 7.29A | H | $(CH_2)_4C(=O)OC_2H_5$ | $C_3H_7(iso)$ | |
| 7.30A | H | $N=C(pyrid-3-yl)H$ | $C_3H_7(iso)$ | |
| 7.31A | H | $N=C(C_6H_5)H$ | $C_3H_7(iso)$ | |
| 7.32A | H | $CH_2OCH_3$ | $C_3H_7(iso)$ | |
| 7.33A | H | $CH_2OC_2H_5$ | $C_3H_7(iso)$ | |
| 7.34A | H | $CH_2CH_2OC_2H_5$ | $C_3H_7(iso)$ | |
| 7.35A | H | $CH_2CH_2Cl$ | $C_3H_7(iso)$ | |
| 7.36A | H | $CHF_2$ | $C_3H_7(iso)$ | |
| 7.37A | H | $CF_2CHF_2$ | $C_3H_7(iso)$ | |
| 7.38A | H | $CH_2SCH_3$ | $C_3H_7(iso)$ | |
| 7.39A | $CH_3$ | H | $C_3H_7(iso)$ | |
| 7.40A | $CH_3$ | $CH_3$ | $C_3H_7(iso)$ | |
| 7.41A | $CH_2CH=CH_2$ | $CH_2CH=CH_2$ | $C_3H_7(iso)$ | |
| 7.42A | $CH_2C(Br)=CH_2$ | $CH_2C(Br)=CH_2$ | $C_3H_7(iso)$ | |
| 7.43A | H | $C(=O)CH_2OCH_3$ | $C_3H_7(iso)$ | |
| 7.44A | H | $C(=O)CH_2CH_2CH_3$ | $C_3H_7(iso)$ | |
| 7.45A | $CH_3$ | $C(=O)CH_2OCH_3$ | $C_3H_7(iso)$ | |
| 7.46A | $CH_3$ | $C(=O)CH(CH_3)_2$ | $C_3H_7(iso)$ | |
| 8.1A | H | H | $C_3H_5(cyclo)$ | 183–184° |
| 8.2A | H | $CH_3$ | $C_3H_5(cyclo)$ | 97–100° |
| 8.3A | H | $C_2H_5$ | $C_3H_5(cyclo)$ | 91–93° |
| 8.4A | H | $C_3H_5(cyclo)$ | $C_3H_5(cyclo)$ | 74–82° |
| 8.5A | H | $C_3H_7(n)$ | $C_3H_5(cyclo)$ | 80–82° |
| 8.6A | H | $C_3H_7(i)$ | $C_3H_5(cyclo)$ | |
| 8.7A | H | $C_4H_9(n)$ | $C_3H_5(cyclo)$ | 75–77° |
| 8.8A | H | $C_4H_9(t)$ | $C_3H_5(cyclo)$ | |
| 8.9A | H | $CH_2CH=CH_2$ | $C_3H_5(cyclo)$ | |
| 8.10A | H | $CH_2C(CH_3)=CH_2$ | $C_3H_5(cyclo)$ | |
| 8.11A | H | $CH_2C(Br)=CH_2$ | $C_3H_5(cyclo)$ | |
| 8.12A | H | $CH_2C\equiv CH$ | $C_3H_5(cyclo)$ | |
| 8.13A | H | $CH_2C(=O)CH_3$ | $C_3H_5(cyclo)$ | |
| 8.14A | H | $CH_2C(=O)C_2H_5$ | $C_3H_5(cyclo)$ | |
| 8.15A | H | $C(=O)CH_3$ | $C_3H_5(cyclo)$ | |
| 8.16A | H | $C(=O)C_2H_5$ | $C_3H_5(cyclo)$ | |
| 8.17A | H | $C(=O)C_3H_7(i)$ | $C_3H_5(cyclo)$ | |
| 8.18A | H | $C(=O)OC_2H_5$ | $C_3H_5(cyclo)$ | |
| 8.19A | H | $C(=O)OC_2H_5$ | $C_3H_5(cyclo)$ | |
| 8.20A | H | $C(=O)N(CH_3)_2$ | $C_3H_5(cyclo)$ | |
| 8.21A | H | $C(=O)N(OCH_3)CH_3$ | $C_3H_5(cyclo)$ | |
| 8.22A | H | $CH_2CH(OCH_3)_2$ | $C_3H_5(cyclo)$ | |
| 8.23A | H | $CH_2CH(OC_2H_5)_2$ | $C_3H_5(cyclo)$ | |
| 8.24A | H | $CH_2CH_2OCH_3$ | $C_3H_5(cyclo)$ | |
| 8.25A | H | $CH_2CN$ | $C_3H_5(cyclo)$ | |
| 8.26A | H | $CH_2C(=O)OC_2H_5$ | $C_3H_5(cyclo)$ | |
| 8.27A | H | $CH_2CH_2C(=O)OC_2H_5$ | $C_3H_5(cyclo)$ | |
| 8.28A | H | $(CH_2)_3C(=O)OC_2H_5$ | $C_3H_5(cyclo)$ | |
| 8.29A | H | $(CH_2)_4C(=O)OC_2H_5$ | $C_3H_5(cyclo)$ | |
| 8.30A | H | $N=C(pyrid-3-yl)H$ | $C_3H_5(cyclo)$ | |
| 8.31A | H | $N=C(C_6H_5)H$ | $C_3H_5(cyclo)$ | |
| 8.32A | H | $CH_2OCH_3$ | $C_3H_5(cyclo)$ | |
| 8.33A | H | $CH_2OC_2H_5$ | $C_3H_5(cyclo)$ | |
| 8.34A | H | $CH_2CH_2OC_2H_5$ | $C_3H_5(cyclo)$ | |
| 8.35A | H | $CH_2CH_2Cl$ | $C_3H_5(cyclo)$ | |
| 8.36A | H | $CHF_2$ | $C_3H_5(cyclo)$ | |
| 8.37A | H | $CF_2CHF_2$ | $C_3H_5(cyclo)$ | |
| 8.38A | H | $CH_2SCH_3$ | $C_3H_5(cyclo)$ | |

TABLE 2-continued

| Compound No. | $R_2$ | $R_3$ | $R_1$ | Physical Data |
|---|---|---|---|---|
| 8.39A | $CH_3$ | H | $C_3H_5$(cyclo) | |
| 8.40A | $CH_3$ | $CH_3$ | $C_3H_5$(cyclo) | |
| 8.41A | $CH_2CH=CH_2$ | $CH_2CH=CH_2$ | $C_3H_5$(cyclo) | |
| 8.42A | $CH_2C(Br)=CH_2$ | $CH_2C(Br)=CH_2$ | $C_3H_5$(cyclo) | |
| 8.43A | H | $C(=O)CH_2OCH_3$ | $C_3H_5$(cyclo) | |
| 8.44A | H | $C(=O)CH_2CH_2CH_3$ | $C_3H_5$(cyclo) | |
| 8.45A | $CH_3$ | $C(=O)CH_2OCH_3$ | $C_3H_5$(cyclo) | |
| 8.46A | $CH_3$ | $C(=O)CH(CH_3)_2$ | $C_3H_5$(cyclo) | |
| 9.1A | H | H | $C(CH_3)_3$ | 197–200° |
| 9.2A | H | $CH_3$ | $C(CH_3)_3$ | 100–105° |
| 9.3A | H | $C_2H_5$ | $C(CH_3)_3$ | |
| 9.4A | H | $C_3H_5$(cyclo) | $C(CH_3)_3$ | |
| 9.5A | H | $C_3H_7$(n) | $C(CH_3)_3$ | |
| 9.6A | H | $C_3H_7$(i) | $C(CH_3)_3$ | |
| 9.7A | H | $C_4H_9$(n) | $C(CH_3)_3$ | |
| 9.8A | H | $C_4H_9$(t) | $C(CH_3)_3$ | |
| 9.9A | H | $CH_2CH=CH_2$ | $C(CH_3)_3$ | |
| 9.10A | H | $CH_2C(CH_3)=CH_2$ | $C(CH_3)_3$ | |
| 9.11A | H | $CH_2C(Br)=CH_2$ | $C(CH_3)_3$ | |
| 9.12A | H | $CH_2C\equiv CH$ | $C(CH_3)_3$ | |
| 9.13A | H | $CH_2C(=O)CH_3$ | $C(CH_3)_3$ | |
| 9.14A | H | $CH_2C(=O)C_2H_5$ | $C(CH_3)_3$ | |
| 9.15A | H | $C(=O)CH_3$ | $C(CH_3)_3$ | |
| 9.16A | H | $C(=O)C_2H_5$ | $C(CH_3)_3$ | |
| 9.17A | H | $C(=O)C_3H_7$(i) | $C(CH_3)_3$ | |
| 9.18A | H | $C(=O)OC_2H_5$ | $C(CH_3)_3$ | |
| 9.19A | H | $C(=O)OC_2H_5$ | $C(CH_3)_3$ | |
| 9.20A | H | $C(=O)N(CH_3)_2$ | $C(CH_3)_3$ | |
| 9.21A | H | $C(=O)N(OCH_3)CH_3$ | $C(CH_3)_3$ | |
| 9.22A | H | $CH_2CH(OCH_3)_2$ | $C(CH_3)_3$ | |
| 9.23A | H | $CH_2CH(OC_2H_5)_2$ | $C(CH_3)_3$ | |
| 9.24A | H | $CH_2CH_2OCH_3$ | $C(CH_3)_3$ | |
| 9.25A | H | $CH_2CN$ | $C(CH_3)_3$ | |
| 9.26A | H | $CH_2C(=O)OC_2H_5$ | $C(CH_3)_3$ | |
| 9.27A | H | $CH_2CH_2C(=O)OC_2H_5$ | $C(CH_3)_3$ | |
| 9.28A | H | $(CH_2)_3C(=O)OC_2H_5$ | $C(CH_3)_3$ | |
| 9.29A | H | $(CH_2)_4C(=O)OC_2H_5$ | $C(CH_3)_3$ | |
| 9.30A | H | $N=C(pyrid-3-yl)H$ | $C(CH_3)_3$ | |
| 9.31A | H | $N=C(C_6H_5)H$ | $C(CH_3)_3$ | |
| 9.32A | H | $CH_2OCH_3$ | $C(CH_3)_3$ | |
| 9.33A | H | $CH_2OC_2H_5$ | $C(CH_3)_3$ | |
| 9.34A | H | $CH_2CH_2OC_2H_5$ | $C(CH_3)_3$ | |
| 9.35A | H | $CH_2CH_2Cl$ | $C(CH_3)_3$ | |
| 9.36A | H | $CHF_2$ | $C(CH_3)_3$ | |
| 9.37A | H | $CF_2CHF_2$ | $C(CH_3)_3$ | |
| 9.38A | H | $CH_2SCH_3$ | $C(CH_3)_3$ | |
| 9.39A | $CH_3$ | H | $C(CH_3)_3$ | |
| 9.40A | $CH_3$ | $CH_3$ | $C(CH_3)_3$ | |
| 9.41A | $CH_2CH=CH_2$ | $CH_2CH=CH_2$ | $C(CH_3)_3$ | |
| 9.42A | $CH_2C(Br)=CH_2$ | $CH_2C(Br)=CH_2$ | $C(CH_3)_3$ | |
| 9.43A | H | $C(=O)CH_2OCH_3$ | $C(CH_3)_3$ | |
| 9.44A | H | $C(=O)CH_2CH_2CH_3$ | $C(CH_3)_3$ | |
| 9.45A | $CH_3$ | $C(=O)CH_2OCH_3$ | $C(CH_3)_3$ | |
| 9.46A | $CH_3$ | $C(=O)CH(CH_3)_2$ | $C(CH_3)_3$ | |
| 10.1A | H | H | $CH_2OCH_3$ | |
| 10.2A | H | $CH_3$ | $CH_2OCH_3$ | |
| 10.3A | H | $C_2H_5$ | $CH_2OCH_3$ | |
| 10.4A | H | $C_3H_5$(cyclo) | $CH_2OCH_3$ | |
| 10.5A | H | $C_3H_7$(n) | $CH_2OCH_3$ | |
| 10.6A | H | $C_3H_7$(i) | $CH_2OCH_3$ | |
| 10.7A | H | $C_4H_9$(n) | $CH_2OCH_3$ | |
| 10.8A | H | $C_4H_9$(t) | $CH_2OCH_3$ | |
| 10.9A | H | $CH_2CH=CH_2$ | $CH_2OCH_3$ | |
| 10.10A | H | $CH_2C(CH_3)=CH_2$ | $CH_2OCH_3$ | |
| 10.11A | H | $CH_2C(Br)=CH_2$ | $CH_2OCH_3$ | |
| 10.12A | H | $CH_2C\equiv CH$ | $CH_2OCH_3$ | |
| 10.13A | H | $CH_2C(=O)CH_3$ | $CH_2OCH_3$ | |
| 10.14A | H | $CH_2C(=O)C_2H_5$ | $CH_2OCH_3$ | |

TABLE 2-continued

| Compound No. | $R_2$ | $R_3$ | $R_1$ | Physical Data |
|---|---|---|---|---|
| 10.15A | H | $C(=O)CH_3$ | $CH_2OCH_3$ | |
| 10.16A | H | $C(=O)C_2H_5$ | $CH_2OCH_3$ | |
| 10.17A | H | $C(=O)C_3H_7(i)$ | $CH_2OCH_3$ | |
| 10.18A | H | $C(=O)OC_2H_5$ | $CH_2OCH_3$ | |
| 10.19A | H | $C(=O)OC_2H_5$ | $CH_2OCH_3$ | |
| 10.20A | H | $C(=O)N(CH_3)_2$ | $CH_2OCH_3$ | |
| 10.21A | H | $C(=O)N(OCH_3)CH_3$ | $CH_2OCH_3$ | |
| 10.22A | H | $CH_2CH(OCH_3)_2$ | $CH_2OCH_3$ | |
| 10.23A | H | $CH_2CH(OC_2H_5)_2$ | $CH_2OCH_3$ | |
| 10.24A | H | $CH_2CH_2OCH_3$ | $CH_2OCH_3$ | |
| 10.25A | H | $CH_2CN$ | $CH_2OCH_3$ | |
| 10.26A | H | $CH_2C(=O)OC_2H_5$ | $CH_2OCH_3$ | |
| 10.27A | H | $CH_2CH_2C(=O)OC_2H_5$ | $CH_2OCH_3$ | |
| 10.28A | H | $(CH_2)_3C(=O)OC_2H_5$ | $CH_2OCH_3$ | |
| 10.29A | H | $(CH_2)_4C(=O)OC_2H_5$ | $CH_2OCH_3$ | |
| 10.30A | H | $N=C(pyrid-3-yl)H$ | $CH_2OCH_3$ | |
| 10.31A | H | $N=C(C_6H_5)H$ | $CH_2OCH_3$ | |
| 10.32A | H | $CH_2OCH_3$ | $CH_2OCH_3$ | |
| 10.33A | H | $CH_2OC_2H_5$ | $CH_2OCH_3$ | |
| 10.34A | H | $CH_2CH_2OC_2H_5$ | $CH_2OCH_3$ | |
| 10.35A | H | $CH_2CH_2Cl$ | $CH_2OCH_3$ | |
| 10.36A | H | $CHF_2$ | $CH_2OCH_3$ | |
| 10.37A | H | $CF_2CHF_2$ | $CH_2OCH_3$ | |
| 10.38A | H | $CH_2SCH_3$ | $CH_2OCH_3$ | |
| 10.39A | $CH_3$ | H | $CH_2OCH_3$ | |
| 10.40A | $CH_3$ | $CH_3$ | $CH_2OCH_3$ | |
| 10.41A | $CH_2CH=CH_2$ | $CH_2CH=CH_2$ | $CH_2OCH_3$ | |
| 10.42A | $CH_2C(Br)=CH_2$ | $CH_2C(Br)=CH_2$ | $CH_2OCH_3$ | |
| 10.43A | H | $C(=O)CH_2OCH_3$ | $CH_2OCH_3$ | |
| 10.44A | H | $C(=O)CH_2CH_2CH_3$ | $CH_2OCH_3$ | |
| 10.45A | $CH_3$ | $C(=O)CH_2OCH_3$ | $CH_2OCH_3$ | |
| 10.46A | $CH_3$ | $C(=O)CH(CH_3)_2$ | $CH_2OCH_3$ | |
| 11.1A | H | H | $CH_2OC_2H_5$ | |
| 11.2A | H | $CH_3$ | $CH_2OC_2H_5$ | |
| 11.3A | H | $C_2H_5$ | $CH_2OC_2H_5$ | |
| 11.4A | H | $C_3H_5(cyclo)$ | $CH_2OC_2H_5$ | |
| 11.5A | H | $C_3H_7(n)$ | $CH_2OC_2H_5$ | |
| 11.6A | H | $C_3H_7(i)$ | $CH_2OC_2H_5$ | |
| 11.7A | H | $C_4H_9(n)$ | $CH_2OC_2H_5$ | |
| 11.8A | H | $C_4H_9(t)$ | $CH_2OC_2H_5$ | |
| 11.9A | H | $CH_2CH=CH_2$ | $CH_2OC_2H_5$ | |
| 11.10A | H | $CH_2C(CH_3)=CH_2$ | $CH_2OC_2H_5$ | |
| 11.11A | H | $CH_2C(Br)=CH_2$ | $CH_2OC_2H_5$ | |
| 11.12A | H | $CH_2C\equiv CH$ | $CH_2OC_2H_5$ | |
| 11.13A | H | $CH_2C(=O)CH_3$ | $CH_2OC_2H_5$ | |
| 11.14A | H | $CH_2C(=O)C_2H_5$ | $CH_2OC_2H_5$ | |
| 11.15A | H | $C(=O)CH_3$ | $CH_2OC_2H_5$ | |
| 11.16A | H | $C(=O)C_2H_5$ | $CH_2OC_2H_5$ | |
| 11.17A | H | $C(=O)C_3H_7(i)$ | $CH_2OC_2H_5$ | |
| 11.18A | H | $C(=O)OC_2H_5$ | $CH_2OC_2H_5$ | |
| 11.19A | H | $C(=O)OC_2H_5$ | $CH_2OC_2H_5$ | |
| 11.20A | H | $C(=O)N(CH_3)_2$ | $CH_2OC_2H_5$ | |
| 11.21A | H | $C(=O)N(OCH_3)CH_3$ | $CH_2OC_2H_5$ | |
| 11.22A | H | $CH_2CH(OCH_3)_2$ | $CH_2OC_2H_5$ | |
| 11.23A | H | $CH_2CH(OC_2H_5)_2$ | $CH_2OC_2H_5$ | |
| 11.24A | H | $CH_2CH_2OCH_3$ | $CH_2OC_2H_5$ | |
| 11.25A | H | $CH_2CN$ | $CH_2OC_2H_5$ | |
| 11.26A | H | $CH_2C(=O)OC_2H_5$ | $CH_2OC_2H_5$ | |
| 11.27A | H | $CH_2CH_2C(=O)OC_2H_5$ | $CH_2OC_2H_5$ | |
| 11.28A | H | $(CH_2)_3C(=O)OC_2H_5$ | $CH_2OC_2H_5$ | |
| 11.29A | H | $(CH_2)_4C(=O)OC_2H_5$ | $CH_2OC_2H_5$ | |
| 11.30A | H | $N=C(pyrid-3-yl)H$ | $CH_2OC_2H_5$ | |
| 11.31A | H | $N=C(C_6H_5)H$ | $CH_2OC_2H_5$ | |
| 11.32A | H | $CH_2OCH_3$ | $CH_2OC_2H_5$ | |
| 11.33A | H | $CH_2OC_2H_5$ | $CH_2OC_2H_5$ | |
| 11.34A | H | $CH_2CH_2OC_2H_5$ | $CH_2OC_2H_5$ | |
| 11.35A | H | $CH_2CH_2Cl$ | $CH_2OC_2H_5$ | |
| 11.36A | H | $CHF_2$ | $CH_2OC_2H_5$ | |
| 11.37A | H | $CF_2CHF_2$ | $CH_2OC_2H_5$ | |

TABLE 2-continued $$\underset{R_3}{\overset{R_1}{\underset{\underset{O}{\|}}{\overset{}{N}}}}\underset{NH_2}{\overset{R_2}{N}}$$

| Compound No. | $R_2$ | $R_3$ | $R_1$ | Physical Data |
|---|---|---|---|---|
| 11.38A | H | $CH_2SCH_3$ | $CH_2OC_2H_5$ | |
| 11.39A | $CH_3$ | H | $CH_2OC_2H_5$ | |
| 11.40A | $CH_3$ | $CH_3$ | $CH_2OC_2H_5$ | |
| 11.41A | $CH_2CH=CH_2$ | $CH_2CH=CH_2$ | $CH_2OC_2H_5$ | |
| 11.42A | $CH_2C(Br)=CH_2$ | $CH_2C(Br)=CH_2$ | $CH_2OC_2H_5$ | |
| 11.43A | H | $C(=O)CH_2OCH_3$ | $CH_2OC_2H_5$ | |
| 11.44A | H | $C(=O)CH_2CH_2CH_3$ | $CH_2OC_2H_5$ | |
| 11.45A | $CH_3$ | $C(=O)CH_2OCH_3$ | $CH_2OC_2H_5$ | |
| 11.46A | $CH_3$ | $C(=O)CH(CH_3)_2$ | $CH_2OC_2H_5$ | |
| 12.1A | H | H | $CH_2SCH_3$ | |
| 12.2A | H | $CH_3$ | $CH_2SCH_3$ | |
| 12.3A | H | $C_2H_5$ | $CH_2SCH_3$ | |
| 12.4A | H | $C_3H_5$(cyclo) | $CH_2SCH_3$ | |
| 12.5A | H | $C_3H_7$(n) | $CH_2SCH_3$ | |
| 12.6A | H | $C_3H_7$(i) | $CH_2SCH_3$ | |
| 12.7A | H | $C_4H_9$(n) | $CH_2SCH_3$ | |
| 12.8A | H | $C_4H_9$(t) | $CH_2SCH_3$ | |
| 12.9A | H | $CH_2CH=CH_2$ | $CH_2SCH_3$ | |
| 12.10A | H | $CH_2C(CH_3)=CH_2$ | $CH_2SCH_3$ | |
| 12.11A | H | $CH_2C(Br)=CH_2$ | $CH_2SCH_3$ | |
| 12.12A | H | $CH_2C\equiv CH$ | $CH_2SCH_3$ | |
| 12.13A | H | $CH_2C(=O)CH_3$ | $CH_2SCH_3$ | |
| 12.14A | H | $CH_2C(=O)C_2H_5$ | $CH_2SCH_3$ | |
| 12.15A | H | $C(=O)CH_3$ | $CH_2SCH_3$ | |
| 12.16A | H | $C(=O)C_2H_5$ | $CH_2SCH_3$ | |
| 12.17A | H | $C(=O)C_3H_7$(i) | $CH_2SCH_3$ | |
| 12.18A | H | $C(=O)OC_2H_5$ | $CH_2SCH_3$ | |
| 12.19A | H | $C(=O)OC_2H_5$ | $CH_2SCH_3$ | |
| 12.20A | H | $C(=O)N(CH_3)_2$ | $CH_2SCH_3$ | |
| 12.21A | H | $C(=O)N(OCH_3)CH_3$ | $CH_2SCH_3$ | |
| 12.22A | H | $CH_2CH(OCH_3)_2$ | $CH_2SCH_3$ | |
| 12.23A | H | $CH_2CH(OC_2H_5)_2$ | $CH_2SCH_3$ | |
| 12.24A | H | $CH_2CH_2OCH_3$ | $CH_2SCH_3$ | |
| 12.25A | H | $CH_2CN$ | $CH_2SCH_3$ | |
| 12.26A | H | $CH_2C(=O)OC_2H_5$ | $CH_2SCH_3$ | |
| 12.27A | H | $CH_2CH_2C(=O)OC_2H_5$ | $CH_2SCH_3$ | |
| 12.28A | H | $(CH_2)_3C(=O)OC_2H_5$ | $CH_2SCH_3$ | |
| 12.29A | H | $(CH_2)_4C(=O)OC_2H_5$ | $CH_2SCH_3$ | |
| 12.30A | H | $N=C$(pyrid-3-yl)H | $CH_2SCH_3$ | |
| 12.31A | H | $N=C(C_6H_5)H$ | $CH_2SCH_3$ | |
| 12.32A | H | $CH_2OCH_3$ | $CH_2SCH_3$ | |
| 12.33A | H | $CH_2OC_2H_5$ | $CH_2SCH_3$ | |
| 12.34A | H | $CH_2CH_2OC_2H_5$ | $CH_2SCH_3$ | |
| 12.35A | H | $CH_2CH_2Cl$ | $CH_2SCH_3$ | |
| 12.36A | H | $CHF_2$ | $CH_2SCH_3$ | |
| 12.37A | H | $CF_2CHF_2$ | $CH_2SCH_3$ | |
| 12.38A | H | $CH_2SCH_3$ | $CH_2SCH_3$ | |
| 12.39A | $CH_3$ | H | $CH_2SCH_3$ | |
| 12.40A | $CH_3$ | $CH_3$ | $CH_2SCH_3$ | |
| 12.41A | $CH_2CH=CH_2$ | $CH_2CH=CH_2$ | $CH_2SCH_3$ | |
| 12.42A | $CH_2C(Br)=CH_2$ | $CH_2C(Br)=CH_2$ | $CH_2SCH_3$ | |
| 12.43A | H | $C(=O)CH_2OCH_3$ | $CH_2SCH_3$ | |
| 12.44A | H | $C(=O)CH_2CH_2CH_3$ | $CH_2SCH_3$ | |
| 12.45A | $CH_3$ | $C(=O)CH_2OCH_3$ | $CH_2SCH_3$ | |
| 12.46A | $CH_3$ | $C(=O)CH(CH_3)_2$ | $CH_2SCH_3$ | |

Example H8: 2,3-Dihydro-3-methyl-2-oxo-1-pyrid-3-ylmethyleneamino-4-tert-butyl-1H-imidazole (compound no. 9.2 in table 9).

4.3 g of 3-formylpyridine and two drops of concentrated hydrochloric acid are added to a solution of 6.8 g of 1-amino-2,3-dihydro-3-methyl-2-oxo-4-tert-butyl-1H-imidazole in 50 ml of ethanol. The reaction mixture is refluxed for 30 minutes with stirring and then substantially concentrated. The liquid residue is dissolved in a small amount of diethyl ether, and the solution is cooled to 0°. The crystals which have separated out are filtered off with suction and dried. This gives the title compound which melts at 116°–121°.

Example H9: 2,3-Dihydro-2-oxo-1-pyrid-3-ylmethyleneamino-4-tert-butyl-1H-imidazole (compound no. 9.1 in table 9).

5.4 g of 3-formylpyridine and three drops of concentrated hydrochloric acid are added to a solution of 7.8 g of 1-amino-2,3-dihydro-2-oxo4-tert-butyl-1H-imidazole in 50 ml of ethanol. The reaction mixture is refluxed for 30 minutes with stirring and then cooled to room temperature, upon which the mixture starts to crystallize. To complete the crystal precipitation process, 100 ml of diethyl ether are added to the mixture. The crystallizate is filtered off with suction, triturated with acetonitrile, again filtered off with suction and then dried. This gives the title compound which melts at 255°–256°.

Example H10: 2,3-Dihydro-4-methyl-2-oxo-1-pyrid-3-ylmethyleneamino-1H-imidazole (compound no. 4.1 in table 4).

A solution of 156 g of 3-acetylmethyl-2,3-dihydro-5-methyl-2-oxo-1,3,4-oxadiazole in 600 ml of acetonitrile is treated with 170 g of aqueous ammonia solution (30%), and the mixture is stirred for one hour at 80° in an autoclave. A pressure of approximately 8 bar is in this case established. The resulting suspension is evaporated, the residue is dissolved in 500 ml of methanol, and 40 g of gaseous HCl are passed into the solution at 50°. The reaction mixture is stirred for 30 minutes at 50°, and 107 g of 3-formylpyridine are then added dropwise at the same temperature. The reaction mixture is stirred for a further 30 minutes at 50°, then cooled to 0°, and filtered with suction. The filter cake, consisting of 2,3-dihydro-2-oxo-1-pyrid-3-ylmethyleneamino-4-tert-butyl-1H-imidazole hydrochloride (compound no. 4.1.1 in table 4), is dissolved in water at room temperature. The pH of the solution is brought to approximately 7 using aqueous sodium hydroxide solution (30%), during which process a precipitation of crystals is observed at a pH of approximately 3. The crystals are filtered off with suction and dried in vacuo, yielding the title compound melting at 200°–202°.

Example H11: 2,3-Dihydro-3,4-dimethyl-2-oxo-1-pyrid-3-ylmethyleneamino-1H-imizadole hydrochloride (compound no. 4.2.1 in table 4).

8.2 g of 3-formylpyridine are added to a suspension of 11.4 g of 1-amino-2,3-dihydro-3,4-dimethyl-2-oxo-1H-imidazole hydrochloride in 40 ml of ethanol. The reaction mixture is stirred for 14 hours and then filtered, and the filter cake is washed with a small amount of cold ethanol and dried, yielding the title salt melting above 240°.

Example H12: 2,3-Dihydro-3,4-dimethyl-2-oxo-1-pyrid-3-ylmethyleneamino-1H-imidazole (compound no. 4.2 in table 4).

12.6 g of 2,3-dihydro-3,4-dimethyl-2-oxo-1-pyrid-3-ylmethyleneamino-1H-imidazole hydrochloride are dissolved in 150 ml of water. The solution is saturated with sodium chloride and treated with 100 ml of tetrahydrofuran. The mixture is then rendered weakly alkaline using aqueous sodium hydroxide solution (30%). The phases are separated, and the aqueous phase is extracted nine times using in each case 100 ml of tetrahydrofuran. The combined tetrahydrofuran phases are dried using magnesium sulfate and evaporated, yielding the rifle compound in the form of yellow crystals melting at 186°–187°.

Example H13: 2,3-Dihydro-3-ethylcarbonylmethyl-4-methyl-2-oxo-1-pyrid-3-ylmethyleneamino-1H-imidazole (compound no. 4.14 in table 4).

0.72 g of sodium hydride are added to a suspension of 4.1 g of 2,3-dihydro-4-methyl-2-oxo-1-pyrid-3-ylmethyleneamino-1H-imidazole in 80 ml of N,N-dimethylformamide. The mixture is heated to 50°, treated with a solution of 3.78 g of 1-bromo-2-oxo-butane in 20 ml of N,N-dimethylformamide, and stirred for 30 minutes. The N,N-dimethylformamide is then removed on a rotary evaporator. In a mixer, the residue is mixed intimately with water. The crystals are filtered off, yielding the title compound melting at 183°–184°.

Example H14: 3-Cyanomethyl-2,3-dihydro-4-methyl-2-oxo-1-pyrid-3-ylmethyleneamino-1H-imidazole (compound no. 4.25 in table 4).

0.72 g of sodium hydride are added to a suspension of 4.1 g of 2,3-dihydro-4-methyl-2-oxo-1-pyrid-3-ylmethyleneamino-1H-imidazole in 80 ml of N,N-dimethylformamide. The mixture is heated to 50°, treated with a solution of 1.89 g of chloroacetonitrile in 20 ml of N,N-dimethylformamide, and stirred for 30 minutes. The N,N-dimethylformamide is then removed on a rotary evaporator. In a mixer, the residue is mixed intimately with water. The crystals are filtered off, yielding the title compound melting at 195°–198°.

Example H15: 2,3-Dihydro-3-(4-ethoxycarbonylbut-1-yl)-4-methyl-2-oxo-1-pyrid-3-ylmethyleneamino-1H-imidazole (compound no. 4.29 in table 4).

0.72 g of sodium hydride are added to a suspension of 4.1 g of 2,3-dihydro-4-methyl-2-oxo-1-pyrid-3-ylmethyleneamino-1H-imidazole in 80 ml of N,N-dimethylformamide. The mixture is heated to 50°, treated with a solution of 5.22 g of 1-bromo-4-ethoxy-carbonylbutane in 20 ml of N,N-dimethylformamide, and stirred for 30 minutes. The N,N-dimethylformamide is then removed on a rotary evaporator. The residue is treated with ethyl acetate, during which process sodium bromide precipitates. The mixture is filtered over Celite, and the filtrate is evaporated. The residue is treated with hexane, during which process crystals precipitate. The crystals are filtered off with suction and dried yielding the title compound melting at 74°–76°.

Example H16

Analogously to the procedures described in Examples H8 to H15 also the other compounds listed in tables 3 to 17 can be prepared. The temperatures given in the column "Physical Data" of these tables in each case denote the melting point of the compound in question.

TABLE 3

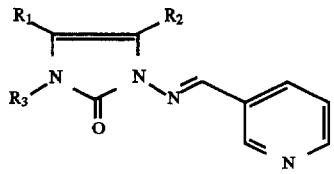

| Compound No. | $R_2$ | $R_3$ | Physical Data |
|---|---|---|---|
| 3.1 | H | H | |
| 3.2 | H | $CH_3$ | |
| 3.3 | H | $C_2H_5$ | |
| 3.4 | H | $C_3H_5$(cyclo) | |
| 3.5 | H | $C_3H_7$(n) | |
| 3.6 | H | $C_3H_7$(i) | |
| 3.7 | H | $C_4H_9$(n) | |
| 3.8 | H | $C_4H_9$(t) | |

TABLE 3-continued

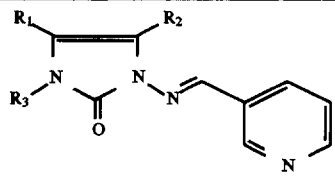

| Compound No. | R$_2$ | R$_3$ | Physical Data |
|---|---|---|---|
| 3.9 | H | CH$_2$CH=CH$_2$ | |
| 3.10 | H | CH$_2$C(CH$_3$)=CH$_2$ | |
| 3.11 | H | CH$_2$C(Br)=CH$_2$ | |
| 3.12 | H | CH$_2$C≡CH | |
| 3.13 | H | CH$_2$C(=O)CH$_3$ | |
| 3.14 | H | CH$_2$C(=O)C$_2$H$_5$ | |
| 3.15 | H | C(=O)CH$_3$ | |
| 3.16 | H | C(=O)C$_2$H$_5$ | |
| 3.17 | H | C(=O)C$_3$H$_7$(i) | |
| 3.18 | H | C(=O)OCH$_3$ | |
| 3.19 | H | C(=O)OC$_2$H$_5$ | |
| 3.20 | H | C(=O)N(CH$_3$)$_2$ | |
| 3.21 | H | C(=O)N(OCH$_3$)CH$_3$ | |
| 3.22 | H | CH$_2$CH(OCH$_3$)$_2$ | |
| 3.23 | H | CH$_2$CH(OC$_2$H$_5$)$_2$ | |
| 3.24 | H | CH$_2$CH$_2$OCH$_3$ | |
| 3.25 | H | CH$_2$CN | |
| 3.26 | H | CH$_2$C(=O)OC$_2$H$_5$ | |
| 3.27 | H | CH$_2$CH$_2$C(=O)OC$_2$H$_5$ | |
| 3.28 | H | (CH$_2$)$_3$C(=O)OC$_2$H$_5$ | |
| 3.29 | H | (CH$_2$)$_4$C(=O)OC$_2$H$_5$ | |
| 3.30 | H | N=C(pyrid-3-yl)H | |
| 3.31 | H | N=C(C$_6$H$_5$)H | |
| 3.32 | H | CH$_2$OCH$_3$ | |
| 3.33 | H | CH$_2$OC$_2$H$_5$ | |
| 3.34 | H | CH$_2$CH$_2$OC$_2$H$_5$ | |
| 3.35 | H | CH$_2$CH$_2$Cl | |
| 3.36 | H | CHF$_2$ | |
| 3.37 | H | CF$_2$CHF$_2$ | |
| 3.38 | H | CH$_2$SCH$_3$ | |
| 3.39 | CH$_3$ | H | |
| 3.40 | CH$_3$ | CH$_3$ | |
| 3.41 | CH$_2$CH=CH$_2$ | CH$_2$CH=CH$_2$ | |
| 3.42 | CH$_2$C(Br)=CH$_2$ | CH$_2$C(Br)=CH$_2$ | |
| 3.43 | H | C(=O)CH$_2$OCH$_3$ | |
| 3.44 | H | C(=O)CH$_2$CH$_2$CH$_3$ | |
| 3.45 | CH$_3$ | C(=O)CH$_2$OCH$_3$ | 157–162° |
| 3.46 | CH$_3$ | C(=O)CH(CH$_3$)$_2$ | 105–107° |
| 3.47 | CH$_3$ | C$_2$H$_5$ | |
| 3.48 | CH$_3$ | C$_3$H$_5$(cyclo) | |
| 3.49 | CH$_3$ | C$_3$H$_7$(n) | |
| 3.50 | CH$_3$ | C$_4$H$_9$(n) | |

TABLE 4

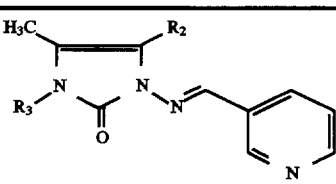

| Compound No. | R$_2$ | R$_3$ | Physical Data |
|---|---|---|---|
| 4.1 | H | H | 200–202° |
| 4.1.1 | Hydrochloride of compound no. 4.1 | | |
| 4.2 | H | CH$_3$ | 186–187° |
| 4.2.1 | Hydrochloride of compound no. 4.2 | | above 240° |
| 4.3 | H | C$_2$H$_5$ | 182–184° |
| 4.4 | H | C$_3$H$_5$(cyclo) | |
| 4.5 | H | C$_3$H$_7$(n) | |
| 4.6 | H | C$_3$H$_7$(i) | |
| 4.7 | H | C$_4$H$_9$(n) | |

TABLE 4-continued

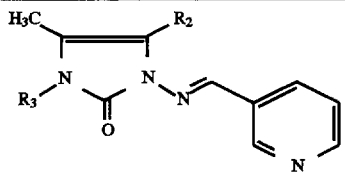

| Compound No. | R$_2$ | R$_3$ | Physical Data |
|---|---|---|---|
| 4.8 | H | C$_4$H$_9$(t) | |
| 4.9 | H | CH$_2$CH=CH$_2$ | 101–105° |
| 4.10 | H | CH$_2$C(CH$_3$)=CH$_2$ | 119–121° |
| 4.11 | H | CH$_2$C(Br)=CH$_2$ | 108–109° |
| 4.12 | H | CH$_2$C≡CH | 156–157° |
| 4.13 | H | CH$_2$C(=O)CH$_3$ | 199–201° |
| 4.14 | H | CH$_2$C(=O)C$_2$H$_5$ | 183–184° |
| 4.15 | H | C(=O)CH$_3$ | 147–150° |
| 4.16 | H | C(=O)C$_2$H$_5$ | 95–103° |
| 4.17 | H | C(=O)C$_3$H$_7$(i) | 102–103° |
| 4.18 | H | C(=O)OCH$_3$ | |
| 4.19 | H | C(=O)OC$_2$H$_5$ | 148–150° |
| 4.20 | H | C(=O)N(CH$_3$)$_2$ | resin |
| 4.21 | H | C(=O)N(OCH$_3$)$_2$ | 93–95° |
| 4.22 | H | CH$_2$CH(OCH$_3$)$_2$ | 115–117° |
| 4.23 | H | CH$_2$CH(OC$_2$H$_5$)$_2$ | 72–73° |
| 4.24 | H | CH$_2$CH$_2$OCH$_3$ | |
| 4.25 | H | CH$_2$CN | 195–198° |
| 4.26 | H | CH$_2$C(=O)OC$_2$H$_5$ | 138–140° |
| 4.27 | H | CH$_2$CH$_2$C(=O)OC$_2$H$_5$ | |
| 4.28 | H | (CH$_2$)$_3$C(=O)OC$_2$H$_5$ | |
| 4.29 | H | (CH$_2$)$_4$C(=O)OC$_2$H$_5$ | 74–76° |
| 4.30 | H | N=C(pyrid-3-yl)H | |
| 4.31 | H | N=C(C$_6$H$_5$)H | |
| 4.32 | H | CH$_2$OCH$_3$ | |
| 4.33 | H | CH$_2$OC$_2$H$_5$ | |
| 4.34 | H | CH$_2$CH$_2$OC$_2$H$_5$ | |
| 4.35 | H | CH$_2$CH$_2$Cl | |
| 4.36 | H | CHF$_2$ | |
| 4.37 | H | CF$_2$CHF$_2$ | |
| 4.38 | H | CH$_2$SCH$_3$ | |
| 4.39 | CH$_3$ | H | |
| 4.40 | CH$_3$ | CH$_3$ | |
| 4.41 | CH$_2$CH=CH$_2$ | CH$_2$CH=CH$_2$ | 116–117° |
| 4.42 | CH$_2$C(Br)=CH$_2$ | CH$_2$C(Br)=CH$_2$ | 87–89° |
| 4.43 | H | C(=O)CH$_2$OCH$_3$ | 162–164° |
| 4.44 | H | C(=O)CH$_2$CH$_2$CH$_3$ | 93–95° |
| 4.45 | CH$_3$ | C(=O)CH$_2$OCH$_3$ | |
| 4.46 | CH$_3$ | C(=O)CH(CH$_3$)$_2$ | |

TABLE 5

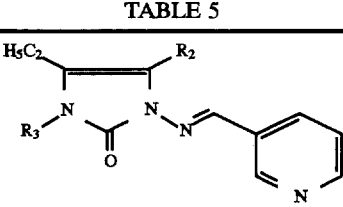

| Compound No. | R$_2$ | R$_3$ | Physical Data |
|---|---|---|---|
| 5.1 | H | H | |
| 5.2 | H | CH$_3$ | |
| 5.3 | H | C$_2$H$_5$ | |
| 5.4 | H | C$_3$H$_5$(cyclo) | |
| 5.5 | H | C$_3$H$_7$(n) | |
| 5.6 | H | C$_3$H$_7$(i) | |
| 5.7 | H | C$_4$H$_9$(n) | |
| 5.8 | H | C$_4$H$_9$(t) | |
| 5.9 | H | CH$_2$CH=CH$_2$ | |
| 5.10 | H | CH$_2$C(CH$_3$)=CH$_2$ | |
| 5.11 | H | CH$_2$C(Br)=CH$_2$ | |

TABLE 5-continued $H_5C_2$ — [pyrazolone ring with $R_2$, $R_3$, N-N=CH-pyridin-3-yl]

| Compound No. | $R_2$ | $R_3$ | Physical Data |
|---|---|---|---|
| 5.12 | H | $CH_2C\equiv CH$ | |
| 5.13 | H | $CH_2C(=O)CH_3$ | |
| 5.14 | H | $CH_2C(=O)C_2H_5$ | |
| 5.15 | H | $C(=O)CH_3$ | |
| 5.16 | H | $C(=O)C_2H_5$ | |
| 5.17 | H | $C(=O)C_3H_7(i)$ | |
| 5.18 | H | $C(=O)OCH_3$ | |
| 5.19 | H | $C(=O)OC_2H_5$ | |
| 5.20 | H | $C(=O)N(CH_3)_2$ | |
| 5.21 | H | $C(=O)N(OCH_3)CH_3$ | |
| 5.22 | H | $CH_2CH(OCH_3)_2$ | |
| 5.23 | H | $CH_2CH(OC_2H_5)_2$ | |
| 5.24 | H | $CH_2CH_2OCH_3$ | |
| 5.25 | H | $CH_2CN$ | |
| 5.26 | H | $CH_2C(=O)OC_2H_5$ | |
| 5.27 | H | $CH_2CH_2C(=O)OC_2H_5$ | |
| 5.28 | H | $(CH_2)_3C(=O)OC_2H_5$ | |
| 5.29 | H | $(CH_2)_4C(=O)OC_2H_5$ | |
| 5.30 | H | $N=C(pyrid-3-yl)H$ | |
| 5.31 | H | $N=C(C_6H_5)H$ | |
| 5.32 | H | $CH_2OCH_3$ | |
| 5.33 | H | $CH_2OC_2H_5$ | |
| 5.34 | H | $CH_2CH_2OC_2H_5$ | |
| 5.35 | H | $CH_2CH_2Cl$ | |
| 5.36 | H | $CHF_2$ | |
| 5.37 | H | $CF_2CHF_2$ | |
| 5.38 | H | $CH_2SCH_3$ | |
| 5.39 | $CH_3$ | H | |
| 5.40 | $CH_3$ | $CH_3$ | |
| 5.41 | $CH_2CH=CH_2$ | $CH_2CH=CH_2$ | |
| 5.42 | $CH_2C(Br)=CH_2$ | $CH_2C(Br)=CH_2$ | |
| 5.43 | H | $C(=O)CH_2OCH_3$ | |
| 5.44 | H | $C(=O)CH_2CH_2CH_3$ | |
| 5.45 | $CH_3$ | $C(=O)CH_2OCH_3$ | |
| 5.46 | $CH_3$ | $C(=O)CH(CH_3)_2$ | |

TABLE 6

$H_3CH_2CH_2C$ — [pyrazolone ring with $R_2$, $R_3$, N-N=CH-pyridin-3-yl]

| Compound No. | $R_2$ | $R_3$ | Physical Data |
|---|---|---|---|
| 6.1 | H | H | |
| 6.2 | H | $CH_3$ | |
| 6.3 | H | $C_2H_5$ | |
| 6.4 | H | $C_3H_5(cyclo)$ | |
| 6.5 | H | $C_3H_7(n)$ | |
| 6.6 | H | $C_3H_7(i)$ | |
| 6.7 | H | $C_4H_9(n)$ | |
| 6.8 | H | $C_4H_9(t)$ | |
| 6.9 | H | $CH_2CH=CH_2$ | |
| 6.10 | H | $CH_2C(CH_3)=CH_2$ | |
| 6.11 | H | $CH_2C(Br)=CH_3$ | |
| 6.12 | H | $CH_2C\equiv CH$ | |
| 6.13 | H | $CH_2C(=O)CH_3$ | |
| 6.14 | H | $CH_2C(=O)C_2H_5$ | |
| 6.15 | H | $C(=O)CH_3$ | |

TABLE 6-continued $H_3CH_2CH_2C$ — [pyrazolone ring with $R_2$, $R_3$, N-N=CH-pyridin-3-yl]

| Compound No. | $R_2$ | $R_3$ | Physical Data |
|---|---|---|---|
| 6.16 | H | $C(=O)C_2H_5$ | |
| 6.17 | H | $C(=O)C_3H_7(i)$ | |
| 6.18 | H | $C(=O)OCH_3$ | |
| 6.19 | H | $C(=O)OC_2H_5$ | |
| 6.20 | H | $C(=O)N(CH_3)_2$ | |
| 6.21 | H | $C(=O)N(OCH_3)CH_3$ | |
| 6.22 | H | $CH_2CH(OCH_3)_2$ | |
| 6.23 | H | $CH_2CH(OC_2H_5)_2$ | |
| 6.24 | H | $CH_2CH_2OCH_3$ | |
| 6.25 | H | $CH_2CN$ | |
| 6.26 | H | $CH_2C(=O)OC_2H_5$ | |
| 6.27 | H | $CH_2CH_2C(=O)OC_2H_5$ | |
| 6.28 | H | $(CH_2)_3C(=O)OC_2H_5$ | |
| 6.29 | H | $(CH_2)_4C(=O)OC_2H_5$ | |
| 6.30 | H | $N=C(pyrid-3-yl)H$ | |
| 6.31 | H | $N=C(C_6H_5)H$ | |
| 6.32 | H | $CH_2OCH_3$ | |
| 6.33 | H | $CH_2OC_2H_5$ | |
| 6.34 | H | $CH_2CH_2OC_2H_5$ | |
| 6.35 | H | $CH_2CH_2Cl$ | |
| 6.36 | H | $CHF_2$ | |
| 6.37 | H | $CF_2CHF_2$ | |
| 6.38 | H | $CH_2SCH_3$ | |
| 6.39 | $CH_3$ | H | |
| 6.40 | $CH_3$ | $CH_3$ | |
| 6.41 | $CH_2CH=CH_2$ | $CH_2CH=CH_2$ | |
| 6.42 | $CH_2C(Br)=CH_2$ | $CH_2C(Br)=CH_2$ | |
| 6.43 | H | $C(=O)CH_2OCH_3$ | |
| 6.44 | H | $C(=O)CH_2CH_2CH_3$ | |
| 6.45 | $CH_3$ | $C(=O)CH_2OCH_3$ | |
| 6.46 | $CH_3$ | $C(=O)CH(CH_3)_2$ | |

TABLE 7

$H_3C(H_3C)HC$ — [pyrazolone ring with $R_2$, $R_3$, N-N=CH-pyridin-3-yl]

| Compound No. | $R_2$ | $R_3$ | Physical Data |
|---|---|---|---|
| 7.1 | H | H | |
| 7.2 | H | $CH_3$ | |
| 7.3 | H | $C_2H_5$ | |
| 7.4 | H | $C_3H_5(cyclo)$ | |
| 7.5 | H | $C_3H_7(n)$ | |
| 7.6 | H | $C_3H_7(i)$ | |
| 7.7 | H | $C_4H_9(n)$ | |
| 7.8 | H | $C_4H_9(t)$ | |
| 7.9 | H | $CH_2CH=CH_2$ | |
| 7.10 | H | $CH_2C(CH_3)=CH_2$ | |
| 7.11 | H | $CH_2C(Br)=CH_3$ | |
| 7.12 | H | $CH_2C\equiv CH$ | |
| 7.13 | H | $CH_2C(=O)CH_3$ | |
| 7.14 | H | $CH_2C(=O)C_2H_5$ | |
| 7.15 | H | $C(=O)CH_3$ | |
| 7.16 | H | $C(=O)C_2H_5$ | |
| 7.17 | H | $C(=O)C_3H_7(i)$ | |
| 7.18 | H | $C(=O)OCH_3$ | |
| 7.19 | H | $C(=O)OC_2H_5$ | |
| 7.20 | H | $C(=O)N(CH_3)_2$ | |

TABLE 7-continued

Structure: H₃C(H₃C)HC- on pyrazole ring with R₂, R₃-N, C=O, N-N=CH-pyridin-3-yl

| Compound No. | R₂ | R₃ | Physical Data |
|---|---|---|---|
| 7.21 | H | C(=O)N(OCH₃)CH₃ | |
| 7.22 | H | CH₂CH(OCH₃)₂ | |
| 7.23 | H | CH₂CH(OC₂H₅)₂ | |
| 7.24 | H | CH₂CH₂OCH₃ | |
| 7.25 | H | CH₂CN | |
| 7.26 | H | CH₂C(=O)OC₂H₅ | |
| 7.27 | H | CH₂CH₂C(=O)OC₂H₅ | |
| 7.28 | H | (CH₂)₃C(=O)OC₂H₅ | |
| 7.29 | H | (CH₂)₄C(=O)OC₂H₅ | |
| 7.30 | H | N=C(pyrid-3-yl)H | |
| 7.31 | H | N=C(C₆H₅)H | |
| 7.32 | H | CH₂OCH₃ | |
| 7.33 | H | CH₂OC₂H₅ | |
| 7.34 | H | CH₂CH₂OC₂H₅ | |
| 7.35 | H | CH₂CH₂Cl | |
| 7.36 | H | CHF₂ | |
| 7.37 | H | CF₂CHF₂ | |
| 7.38 | H | CH₂SCH₃ | |
| 7.39 | CH₃ | H | |
| 7.40 | CH₃ | CH₃ | |
| 7.41 | CH₂CH=CH₂ | CH₂CH=CH₂ | |
| 7.42 | CH₂C(Br)=CH₂ | CH₂C(Br)=CH₂ | |
| 7.43 | H | C(=O)CH₂OCH₃ | |
| 7.44 | H | C(=O)CH₂CH₂CH₃ | |
| 7.45 | CH₃ | C(=O)CH₂OCH₃ | |
| 7.46 | CH₃ | C(=O)CH(CH₃)₂ | |

TABLE 8

Structure: (cyclo)H₅C₃- on pyrazole ring with R₂, R₃-N, C=O, N-N=CH-pyridin-3-yl

| Compound No. | R₂ | R₃ | Physical Data |
|---|---|---|---|
| 8.1 | H | H | 193–194° |
| 8.2 | H | CH₃ | 170–172° |
| 8.3 | H | C₂H₅ | 107–110° |
| 8.4 | H | C₃H₅(cyclo) | 105–106° |
| 8.5 | H | C₃H₇(n) | 82–84° |
| 8.6 | H | C₃H₇(i) | |
| 8.7 | H | C₄H₉(n) | 99–101° |
| 8.8 | H | C₄H₉(t) | |
| 8.9 | H | CH₂CH=CH₂ | |
| 8.10 | H | CH₂C(CH₃)=CH₂ | |
| 8.11 | H | CH₂C(Br)=CH₃ | |
| 8.12 | H | CH₂C≡CH | |
| 8.13 | H | CH₂C(=O)CH₃ | |
| 8.14 | H | CH₂C(=O)C₂H₅ | |
| 8.15 | H | C(=O)CH₃ | |
| 8.16 | H | C(=O)C₂H₅ | |
| 8.17 | H | C(=O)C₃H₇(i) | |
| 8.18 | H | C(=O)OCH₃ | |
| 8.19 | H | C(=O)OC₂H₅ | |
| 8.20 | H | C(=O)N(CH₃)₂ | |
| 8.21 | H | C(=O)N(OCH₃)CH₃ | |
| 8.22 | H | CH₂CH(OCH₃)₂ | |
| 8.23 | H | CH₂CH(OC₂H₅)₂ | |
| 8.24 | H | CH₂CH₂OCH₃ | |
| 8.25 | H | CH₂CN | |

TABLE 8-continued

| Compound No. | R₂ | R₃ | Physical Data |
|---|---|---|---|
| 8.26 | H | CH₂C(=O)OC₂H₅ | |
| 8.27 | H | CH₂CH₂C(=O)OC₂H₅ | |
| 8.28 | H | (CH₂)₃C(=O)OC₂H₅ | |
| 8.29 | H | (CH₂)₄C(=O)OC₂H₅ | |
| 8.30 | H | N=C(pyrid-3-yl)H | |
| 8.31 | H | N=C(C₆H₅)H | |
| 8.32 | H | CH₂OCH₃ | |
| 8.33 | H | CH₂OC₂H₅ | |
| 8.34 | H | CH₂CH₂OC₂H₅ | |
| 8.35 | H | CH₂CH₂Cl | |
| 8.36 | H | CHF₂ | |
| 8.37 | H | CF₂CHF₂ | |
| 8.38 | H | CH₂SCH₃ | |
| 8.39 | CH₃ | H | |
| 8.40 | CH₃ | CH₃ | |
| 8.41 | CH₂CH=CH₂ | CH₂CH=CH₂ | |
| 8.42 | CH₂C(Br)=CH₂ | CH₂C(Br)=CH₂ | |
| 8.43 | H | C(=O)CH₂OCH₃ | |
| 8.44 | H | C(=O)CH₂CH₂CH₃ | |
| 8.45 | CH₃ | C(=O)CH₂OCH₃ | |
| 8.46 | CH₃ | C(=O)CH(CH₃)₂ | |

TABLE 9

Structure: (H₃C)₃C- on pyrazole ring with R₂, R₃-N, C=O, N-N=CH-pyridin-3-yl

| Compound No. | R₂ | R₃ | Physical Data |
|---|---|---|---|
| 9.1 | H | H | 255–256° |
| 9.2 | H | CH₃ | 116–121° |
| 9.3 | H | C₂H₅ | |
| 9.4 | H | C₃H₅(cyclo) | |
| 9.5 | H | C₃H₇(n) | |
| 9.6 | H | C₃H₇(i) | |
| 9.7 | H | C₄H₉(n) | |
| 9.8 | H | C₄H₉(t) | |
| 9.9 | H | CH₂CH=CH₂ | |
| 9.10 | H | CH₂C(CH₃)=CH₂ | |
| 9.11 | H | CH₂C(Br)=CH₃ | |
| 9.12 | H | CH₂C≡CH | |
| 9.13 | H | CH₂C(=O)CH₃ | |
| 9.14 | H | CH₂C(=O)C₂H₅ | |
| 9.15 | H | C(=O)CH₃ | |
| 9.16 | H | C(=O)C₂H₅ | |
| 9.17 | H | C(=O)C₃H₇(i) | |
| 9.18 | H | C(=O)OCH₃ | |
| 9.19 | H | C(=O)OC₂H₅ | |
| 9.20 | H | C(=O)N(CH₃)₂ | |
| 9.21 | H | C(=O)N(OCH₃)CH₃ | |
| 9.22 | H | CH₂CH(OCH₃)₂ | |
| 9.23 | H | CH₂CH(OC₂H₅)₂ | |
| 9.24 | H | CH₂OCH₃ | |
| 9.25 | H | CH₂CN | |
| 9.26 | H | CH₂C(=O)OC₂H₅ | |
| 9.27 | H | CH₂CH₂C(=O)OC₂H₅ | |
| 9.28 | H | (CH₂)₃C(=O)OC₂H₅ | |
| 9.29 | H | (CH₂)₄C(=O)OC₂H₅ | |
| 9.30 | H | N=C(pyrid-3-yl)H | |

TABLE 9-continued

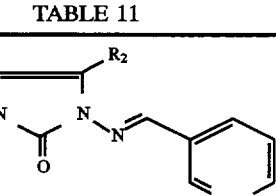

| Compound No. | R₂ | R₃ | Physical Data |
|---|---|---|---|
| 9.31 | H | N=C(C₆H₅)H | |
| 9.32 | H | CH₂OCH₃ | |
| 9.33 | H | CH₂OC₂H₅ | |
| 9.34 | H | CH₂CH₂OC₂H₅ | |
| 9.35 | H | CH₂CH₂Cl | |
| 9.36 | H | CHF₂ | |
| 9.37 | H | CF₂CHF₂ | |
| 9.38 | H | CH₂SCH₃ | |
| 9.39 | CH₃ | H | |
| 9.40 | CH₃ | CH₃ | |
| 9.41 | CH₂CH=CH₂ | CH₂CH=CH₂ | |
| 9.42 | CH₂C(Br)=CH₂ | CH₂C(Br)=CH₂ | |
| 9.43 | H | C(=O)CH₂OCH₃ | |
| 9.44 | H | C(=O)CH₂CH₂CH₃ | |
| 9.45 | CH₃ | C(=O)CH₂OCH₃ | |
| 9.46 | CH₃ | C(=O)CH(CH₃)₂ | |

TABLE 10

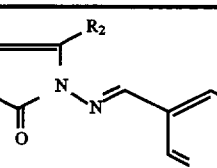

| Compound No. | R₂ | R₃ | Physical Data |
|---|---|---|---|
| 10.1 | H | H | |
| 10.2 | H | CH₃ | |
| 10.3 | H | C₂H₅ | |
| 10.4 | H | C₃H₅(cyclo) | |
| 10.5 | H | C₃H₇(n) | |
| 10.6 | H | C₃H₇(i) | |
| 10.7 | H | C₄H₉(n) | |
| 10.8 | H | C₄H₉(t) | |
| 10.9 | H | CH₂CH=CH₂ | |
| 10.10 | H | CH₂C(CH₃)=CH₂ | |
| 10.11 | H | CH₂C(Br)=CH₃ | |
| 10.12 | H | CH₂C≡CH | |
| 10.13 | H | CH₂C(=O)CH₃ | |
| 10.14 | H | CH₂C(=O)C₂H₅ | |
| 10.15 | H | C(=O)CH₃ | |
| 10.16 | H | C(=O)C₂H₅ | |
| 10.17 | H | C(=O)C₃H₇(i) | |
| 10.18 | H | C(=O)OCH₃ | |
| 10.19 | H | C(=O)OC₂H₅ | |
| 10.20 | H | C(=O)N(CH₃)₂ | |
| 10.21 | H | C(=O)N(OCH₃)CH₃ | |
| 10.22 | H | CH₂CH(OCH₃)₂ | |
| 10.23 | H | CH₂CH(OC₂H₅)₂ | |
| 10.24 | H | CH₂CH₂OCH₃ | |
| 10.25 | H | CH₂CN | |
| 10.26 | H | CH₂C(=O)OC₂H₅ | |
| 10.27 | H | CH₂CH₂C(=O)OC₂H₅ | |
| 10.28 | H | (CH₂)₃C(=O)OC₂H₅ | |
| 10.29 | H | (CH₂)₄C(=O)OC₂H₅ | |
| 10.30 | H | N=C(pyrid-3-yl)H | |
| 10.31 | H | N=C(C₆H₅)H | |
| 10.32 | H | CH₂OCH₃ | |
| 10.33 | H | CH₂OC₂H₅ | |
| 10.34 | H | CH₂CH₂OC₂H₅ | |
| 10.35 | H | CH₂CH₂Cl | |

TABLE 10-continued

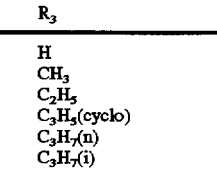

| Compound No. | R₂ | R₃ | Physical Data |
|---|---|---|---|
| 10.36 | H | CHF₂ | |
| 10.37 | H | CF₂CHF₂ | |
| 10.38 | H | CH₂SCH₃ | |
| 10.39 | CH₃ | H | |
| 10.40 | CH₃ | CH₃ | |
| 10.41 | CH₂CH=CH₂ | CH₂CH=CH₂ | |
| 10.42 | CH₂C(Br)=CH₂ | CH₂C(Br)=CH₂ | |
| 10.43 | H | C(=O)CH₂OCH₃ | |
| 10.44 | H | C(=O)CH₂CH₂CH₃ | |
| 10.45 | CH₃ | C(=O)CH₂OCH₃ | |
| 10.46 | CH₃ | C(=O)CH(CH₃)₂ | |

TABLE 11

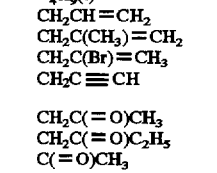

| Compound No. | R₂ | R₃ | Physical Data |
|---|---|---|---|
| 11.1 | H | H | |
| 11.2 | H | CH₃ | |
| 11.3 | H | C₂H₅ | |
| 11.4 | H | C₃H₅(cyclo) | |
| 11.5 | H | C₃H₇(n) | |
| 11.6 | H | C₃H₇(i) | |
| 11.7 | H | C₄H₉(n) | |
| 11.8 | H | C₄H₉(t) | |
| 11.9 | H | CH₂CH=CH₂ | |
| 11.10 | H | CH₂C(CH₃)=CH₂ | |
| 11.11 | H | CH₂C(Br)=CH₃ | |
| 11.12 | H | CH₂C≡CH | |
| 11.13 | H | CH₂C(=O)CH₃ | |
| 11.14 | H | CH₂C(=O)C₂H₅ | |
| 11.15 | H | C(=O)CH₃ | |
| 11.16 | H | C(=O)C₂H₅ | |
| 11.17 | H | C(=O)C₃H₇(i) | |
| 11.18 | H | C(=O)OCH₃ | |
| 11.19 | H | C(=O)OC₂H₅ | |
| 11.20 | H | C(=O)N(CH₃)₂ | |
| 11.21 | H | C(=O)N(OCH₃)CH₃ | |
| 11.22 | H | CH₂CH(OCH₃)₂ | |
| 11.23 | H | CH₂CH(OC₂H₅)₂ | |
| 11.24 | H | CH₂CH₂OCH₃ | |
| 11.25 | H | CH₂CN | |
| 11.26 | H | CH₂C(=O)OC₂H₅ | |
| 11.27 | H | CH₂CH₂C(=O)OC₂H₅ | |
| 11.28 | H | (CH₂)₃C(=O)OC₂H₅ | |
| 11.29 | H | (CH₂)₄C(=O)OC₂H₅ | |
| 11.30 | H | N=C(pyrid-3-yl)H | |
| 11.31 | H | N=C(C₆H₅)H | |
| 11.32 | H | CH₂OCH₃ | |
| 11.33 | H | CH₂OC₂H₅ | |
| 11.34 | H | CH₂CH₂OC₂H₅ | |
| 11.35 | H | CH₂CH₂Cl | |
| 11.36 | H | CHF₂ | |
| 11.37 | H | CF₂CHF₂ | |
| 11.38 | H | CH₂SCH₃ | |
| 11.39 | CH₃ | H | |
| 11.40 | CH₃ | CH₃ | |

TABLE 11-continued

[Structure: pyrazole ring with I₅C₂OH₂C (top-left) and R₂ (top-right) substituents; R₃–N on left, N–N=CH–(3-pyridyl) on right, C=O bridging]

| Compound No. | R₂ | R₃ | Physical Data |
|---|---|---|---|
| 11.41 | CH₂CH=CH₂ | CH₂CH=CH₂ | |
| 11.42 | CH₂C(Br)=CH₂ | CH₂C(Br)=CH₂ | |
| 11.43 | H | C(=O)CH₂OCH₃ | |
| 11.44 | H | C(=O)CH₂CH₂CH₃ | |
| 11.45 | CH₃ | C(=O)CH₂OCH₃ | |
| 11.46 | CH₃ | C(=O)CH(CH₃)₂ | |

TABLE 12

[Structure: pyrazole ring with H₃CSH₂C (top-left) and R₂ (top-right) substituents; R₃–N on left, N–N=CH–(3-pyridyl) on right, C=O bridging]

| Compound No. | R₂ | R₃ | Physical Data |
|---|---|---|---|
| 12.1 | H | H | |
| 12.2 | H | CH₃ | |
| 12.3 | H | C₂H₅ | |
| 12.4 | H | C₃H₅(cyclo) | |
| 12.5 | H | C₃H₇(n) | |
| 12.6 | H | C₃H₇(i) | |
| 12.7 | H | C₄H₉(n) | |
| 12.8 | H | C₄H₉(t) | |
| 12.9 | H | CH₂CH=CH₂ | |
| 12.10 | H | CH₂C(CH₃)=CH₂ | |
| 12.11 | H | CH₂C(Br)=CH₃ | |
| 12.12 | H | CH₂C≡CH | |
| 12.13 | H | CH₂C(=O)CH₃ | |
| 12.14 | H | CH₂C(=O)C₂H₅ | |
| 12.15 | H | C(=O)CH₃ | |
| 12.16 | H | C(=O)C₂H₅ | |
| 12.17 | H | C(=O)C₃H₇(i) | |
| 12.18 | H | C(=O)OCH₃ | |
| 12.19 | H | C(=O)OC₂H₅ | |
| 12.20 | H | C(=O)N(CH₃)₂ | |
| 12.21 | H | C(=O)N(OCH₃)CH₃ | |
| 12.22 | H | CH₂CH(OCH₃)₂ | |
| 12.23 | H | CH₂CH(OC₂H₅)₂ | |
| 12.24 | H | CH₂CH₂OCH₃ | |
| 12.25 | H | CH₂CN | |
| 12.26 | H | CH₂C(=O)OC₂H₅ | |
| 12.27 | H | CH₂CH₂C(=O)OC₂H₅ | |
| 12.28 | H | (CH₂)₃C(=O)OC₂H₅ | |
| 12.29 | H | (CH₂)₄C(=O)OC₂H₅ | |
| 12.30 | H | N=C(pyrid-3-yl)H | |
| 12.31 | H | N=C(C₆H₅)H | |
| 12.32 | H | CH₂OCH₃ | |
| 12.33 | H | CH₂OC₂H₅ | |
| 12.34 | H | CH₂CH₂OC₂H₅ | |
| 12.35 | H | CH₂CH₂Cl | |
| 12.36 | H | CHF₂ | |
| 12.37 | H | CF₂CHF₂ | |
| 12.38 | H | CH₂SCH₃ | |
| 12.39 | CH₃ | H | |
| 12.40 | CH₃ | CH₃ | |
| 12.41 | CH₂CH=CH₂ | CH₂CH=CH₂ | |
| 12.42 | CH₂C(Br)=CH₂ | CH₂C(Br)=CH₂ | |
| 12.43 | H | C(=O)CH₂OCH₃ | |
| 12.44 | H | C(=O)CH₂CH₂CH₃ | |

TABLE 12-continued

| Compound No. | R₂ | R₃ | Physical Data |
|---|---|---|---|
| 12.45 | CH₃ | C(=O)CH₂OCH₃ | |
| 12.46 | CH₃ | C(=O)CH(CH₃)₂ | |

TABLE 13

[Structure: pyrazole ring with R₁ and R₂ substituents; R₃–N on left, N–N(H)–CH₂–(3-pyridyl) on right, C=O bridging]

| Compound No. | R₁ | R₂ | R₃ | Physical Data |
|---|---|---|---|---|
| 13.1 | CH₃ | H | H | |
| 13.2 | CH₃ | H | CH₃ | |
| 13.3 | CH₃ | H | C₂H₅ | |
| 13.4 | CH₃ | H | C₃H₇(i) | |
| 13.5 | CH₃ | H | C₄H₉(t) | |
| 13.6 | CH₃ | CH₃ | CH₃ | |
| 13.7 | C₂H₅ | H | H | |
| 13.8 | C₂H₅ | H | CH₃ | |
| 13.9 | C₂H₅ | H | C₂H₅ | |
| 13.10 | C₂H₅ | H | C₃H₇(i) | |
| 13.11 | C₂H₅ | CH₃ | CH₃ | |
| 13.12 | C₃H₇(i) | H | H | |
| 13.13 | C₃H₇(i) | H | CH₃ | |
| 13.14 | C₃H₇(i) | H | C₂H₅ | |
| 13.15 | C₃H₇(i) | CH₃ | CH₃ | |
| 13.16 | C₄H₉(t) | H | C₃H₇(i) | |
| 13.17 | C₄H₉(t) | CH₃ | H | |
| 13.18 | C₄H₉(t) | H | H | |
| 13.19 | C₄H₉(t) | H | CH₃ | |
| 13.20 | C₄H₉(t) | H | C₂H₅ | |
| 13.21 | C₄H₉(t) | CH₃ | CH₃ | |
| 13.22 | H | CH₃ | C(=O)CH₂OCH₃ | |
| 13.23 | H | CH₃ | C(=O)CH(CH₃)₂ | |

TABLE 14

[Structure: pyrazole ring with R₁ and R₂ substituents; R₃–N on left, N–N(H)–CH₂–(pyridyl N-oxide) on right, C=O bridging]

| Compound No. | R₁ | R₂ | R₃ | Physical Data |
|---|---|---|---|---|
| 14.1 | CH₃ | H | H | |
| 14.2 | CH₃ | H | CH₃ | |
| 14.3 | CH₃ | H | C₂H₅ | |
| 14.4 | CH₃ | H | C₃H₇(i) | |
| 14.5 | CH₃ | H | C₄H₉(t) | |
| 14.6 | CH₃ | CH₃ | CH₃ | |
| 14.7 | C₂H₅ | H | H | |
| 14.8 | C₂H₅ | H | CH₃ | |
| 14.9 | C₂H₅ | H | C₂H₅ | |

TABLE 14-continued

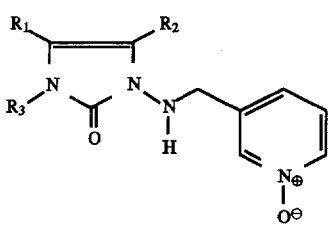

| Compound No. | $R_1$ | $R_2$ | $R_3$ | Physical Data |
|---|---|---|---|---|
| 14.10 | $C_2H_5$ | H | $C_3H_7(i)$ | |
| 14.11 | $C_2H_5$ | $CH_3$ | $CH_3$ | |
| 14.12 | $C_3H_7(i)$ | H | H | |
| 14.13 | $C_3H_7(i)$ | H | $CH_3$ | |
| 14.14 | $C_3H_7(i)$ | H | $C_2H_5$ | |
| 14.15 | $C_3H_7(i)$ | $CH_3$ | $CH_3$ | |
| 14.16 | $C_4H_9(t)$ | H | $C_3H_7(i)$ | |
| 14.17 | $C_4H_9(t)$ | $CH_3$ | H | |
| 14.18 | $C_4H_9(t)$ | H | H | |
| 14.19 | $C_4H_9(t)$ | H | $CH_3$ | |
| 14.20 | $C_4H_9(t)$ | H | $C_2H_5$ | |
| 14.21 | $C_4H_9(t)$ | $CH_3$ | $CH_3$ | |
| 14.22 | H | $CH_3$ | $C(=O)CH_2OCH_3$ | |
| 14.23 | H | $CH_3$ | $C(=O)CH(CH_3)_2$ | |

TABLE 15

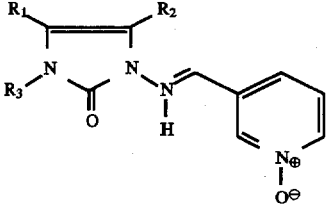

| Compound No. | $R_1$ | $R_2$ | $R_3$ | Physical Data |
|---|---|---|---|---|
| 15.1 | $CH_3$ | H | H | |
| 15.2 | $CH_3$ | H | $CH_3$ | |
| 15.3 | $CH_3$ | H | $C_2H_5$ | |
| 15.4 | $CH_3$ | H | $C_3H_7(i)$ | |
| 15.5 | $CH_3$ | H | $C_4H_9(t)$ | |
| 15.6 | $CH_3$ | $CH_3$ | $CH_3$ | |
| 15.7 | $C_2H_5$ | H | H | |
| 15.8 | $C_2H_5$ | H | $CH_3$ | |
| 15.9 | $C_2H_5$ | H | $C_2H_5$ | |
| 15.10 | $C_2H_5$ | H | $C_3H_7(i)$ | |
| 15.11 | $C_2H_5$ | $CH_3$ | $CH_3$ | |
| 15.12 | $C_3H_7(i)$ | H | H | |
| 15.13 | $C_3H_7(i)$ | H | $CH_3$ | |
| 15.14 | $C_3H_7(i)$ | H | $C_2H_5$ | |
| 15.15 | $C_3H_7(i)$ | $CH_3$ | $CH_3$ | |
| 15.16 | $C_4H_9(t)$ | H | $C_3H_7(i)$ | |
| 15.17 | $C_4H_9(t)$ | $CH_3$ | H | |
| 15.18 | $C_4H_9(t)$ | H | H | |
| 15.19 | $C_4H_9(t)$ | H | $CH_3$ | |
| 15.20 | $C_4H_9(t)$ | H | $C_2H_5$ | |
| 15.21 | $C_4H_9(t)$ | $CH_3$ | $CH_3$ | |
| 15.22 | H | $CH_3$ | $C(=O)CH_2OCH_3$ | |
| 15.23 | H | $CH_3$ | $C(=O)CH(CH_3)_2$ | |

TABLE 16

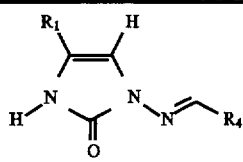

| Compound No. | $R_1$ | $R_4$ | Physical Data |
|---|---|---|---|
| 16.1 | $CH_3$ | thiazol-5-yl | |
| 16.2 | $CH_3$ | pyrimid-5-yl | |
| 16.3 | $CH_3$ | 4,6-dichloropyrimid-5-yl | |
| 16.4 | $CH_3$ | 3-phenylpyrazol-4-yl | |
| 16.5 | $C_2H_5$ | pyrimid-5-yl | |
| 16.6 | $C_3H_5$(cyclo) | pyrimid-5-yl | |
| 16.7 | $C_2H_5$ | 3-phenylpyrazol-4-yl | |
| 16.8 | $CH_3$ | pyrazol-3-yl | |
| 16.9 | $CH_3$ | pyrazin-2-yl | |
| 16.10 | $CH_3$ | pyridazin-4-yl | |
| 16.11 | $CH_3$ | imidazol-4-yl | |
| 16.12 | $CH_3$ | 1-methyl-1H-imidazol-5-yl | |
| 16.13 | $CH_3$ | 1-methylpyrrol-2-yl | |
| 16.14 | $CH_3$ | 1-methyl-1H-pyrazol-4-yl | |
| 16.15 | $CH_3$ | isothiazol-5-yl | |
| 16.16 | $CH_3$ | pyrrol-3-yl | |
| 16.17 | $CH_3$ | pyrrol-2-yl | |
| 16.18 | $CH_3$ | 1-methyl-1H-pyrazol-3-yl | |
| 16.19 | $CH_3$ | pyrazol-4-yl | |
| 16.20 | $CH_3$ | imidazol-2-yl | |
| 16.21 | $CH_3$ | 1-methyl-1H-imidazol-4-yl | |
| 16.22 | $CH_3$ | 4-methylimidazol-5-yl | |
| 16.23 | $CH_3$ | tetrazol-5-yl | |
| 16.24 | $CH_3$ | 2-methylimidazol-4-yl | |
| 16.25 | $CH_3$ | 1-methyl-1H-tetrazol-5-yl | |
| 16.26 | $CH_3$ | 2-methyloxazol-5-yl | |
| 16.27 | $CH_3$ | 2,4-dimethyloxazol-5-yl | |
| 16.28 | $CH_3$ | 2,5-dimethyloxazol-4-yl | |
| 16.29 | $CH_3$ | oxazol-5-yl | |
| 16.30 | $CH_3$ | oxazol-4-yl | |
| 16.31 | $CH_3$ | thiazol-4-yl | |
| 16.32 | $CH_3$ | 2-methylthiazol-4-yl | |
| 16.33 | $CH_3$ | 4-methylthiazol-5-yl | |
| 16.34 | $CH_3$ | 2-methylthiazol-5-yl | |
| 16.35 | $CH_3$ | thiazol-2-yl | |
| 16.36 | $CH_3$ | isoxazol-3-yl | |
| 16.37 | $CH_3$ | isoxazol-5-yl | |
| 16.38 | $CH_3$ | isoxazol-4-yl | |
| 16.39 | $CH_3$ | 3-methylisoxazol-5-yl | |
| 16.40 | $CH_3$ | 5-methylisoxazol-3-yl | |
| 16.41 | $CH_3$ | 3,5-dimethylisoxazol-4-yl | |
| 16.42 | $CH_3$ | isothiazol-3-yl | |
| 16.43 | $CH_3$ | isothiazol-4-yl | |
| 16.44 | $CH_3$ | 3-methylisothiazol-4-yl | |
| 16.45 | $CH_3$ | 3-methylisothiazol-5-yl | |
| 16.46 | $CH_3$ | 1,2,4-triazol-3-yl | |
| 16.47 | $CH_3$ | 1,3,4-oxadiazol-2-yl | |
| 16.48 | $CH_3$ | 2-methyl-1,3,4-oxadiazol-5-yl | |
| 16.49 | $CH_3$ | 1,3,4-thiadiazol-2-yl | |
| 16.50 | $CH_3$ | 2-methyl-1,3,4-thiadiazol-5-yl | |
| 16.51 | $CH_3$ | 1,2,3-thiadiazol-5-yl | |
| 16.52 | $CH_3$ | 1,2,3-thiadiazol-4-yl | |
| 16.53 | $CH_3$ | 5-methyl-1,2,3-thiadiazol-4-yl | |
| 16.54 | $CH_3$ | 1,2,5-thiadiazol-3-yl | |
| 16.55 | $CH_3$ | 3-methyl-1,2,5-thiadiazol-4-yl | |
| 16.56 | $CH_3$ | 1,2,4-thiadiazol-5-yl | |
| 16.57 | $CH_3$ | 1,2,4-thiadiazol-3-yl | |
| 16.58 | $CH_3$ | 1,2,4-oxadiazol-3-yl | |
| 16.59 | $CH_3$ | 1,2,4-oxadiazol-5-yl | |
| 16.60 | $CH_3$ | 1,2,5-oxadiazol-3-yl | |
| 16.61 | $CH_3$ | 3-methyl-1,2,5-oxadiazol-4-yl | |
| 16.62 | $CH_3$ | 1,2,3-triazol-4-yl | |
| 16.63 | $CH_3$ | 1-methyl-1H-1,2,3-triazol-4-yl | |
| 16.64 | $CH_3$ | 4-methyl-1,2,3-triazol-5-yl | |
| 16.65 | $CH_3$ | pyridazin-3-yl | |
| 16.66 | $CH_3$ | 4-methylpyridazin-3-yl | |
| 16.67 | $CH_3$ | 3-methylpyridazin-4-yl | |
| 16.68 | $CH_3$ | 4-methylpyridazin-5-yl | |

TABLE 16-continued

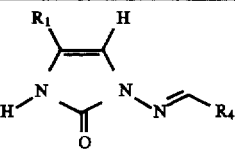

| Compound No. | R₁ | R₄ | Physical Data |
|---|---|---|---|
| 16.69 | CH₃ | 2-methylpyrimid-5-yl | |
| 16.70 | CH₃ | 2,4,6-trimethylpyrimid-5-yl | |
| 16.71 | CH₃ | pyrimid-4-yl | |
| 16.72 | CH₃ | 4-methylpyrimid-6-yl | |
| 16.73 | CH₃ | 2,4-dimethylpyrimid-6-yl | |
| 16.74 | CH₃ | pyrimid-2-yl | |
| 16.75 | CH₃ | 4,6-dimethylpyrimid-2-yl | |
| 16.76 | CH₃ | 2-methylpyrazin-3-yl | |
| 16.77 | CH₃ | 2-methylpyrazin-5-yl | |
| 16.78 | CH₃ | 1,2,4-triazin-5-yl | |
| 16.79 | CH₃ | 3-methyl-1,2,4-triazin-5-yl | |
| 16.80 | CH₃ | 1,3,5-triazin-2-yl | |
| 16.81 | CH₃ | 1,2,4,5-tetrazin-3-yl | |
| 16.82 | C₂H₅ | pyrrol-3-yl | |
| 16.83 | C₂H₅ | 1-methylpyrrol-3-yl | |
| 16.84 | C₂H₅ | pyrrol-2-yl | |
| 16.85 | C₂H₅ | 1-methyl-1H-pyrazol-3-yl | |
| 16.86 | C₂H₅ | pyrazol-3-yl | |
| 16.87 | C₂H₅ | pyrazol-4-yl | |
| 16.88 | C₂H₅ | 1-methyl-1H-pyrazol-4-yl | |
| 16.89 | C₂H₅ | imidazol-2-yl | |
| 16.90 | C₂H₅ | imidazol-4-yl | |
| 16.91 | C₂H₅ | 1-methyl-1H-imidazol-4-yl | |
| 16.92 | C₂H₅ | 1-methyl-1H-imidazol-5-yl | |
| 16.93 | C₂H₅ | 4-methylimidazol-5-yl | |
| 16.94 | C₂H₅ | tetrazol-5-yl | |
| 16.95 | C₂H₅ | 2-methylimidazol-4-yl | |
| 16.96 | C₂H₅ | 1-methyl-1H-tetrazol-5-yl | |
| 16.97 | C₂H₅ | 2-methyloxazol-5-yl | |
| 16.98 | C₂H₅ | 2,4-dimethyloxazol-5-yl | |
| 16.99 | C₂H₅ | 2,5-dimethyloxazol-4-yl | |
| 16.100 | C₂H₅ | oxazol-5-yl | |
| 16.101 | C₂H₅ | oxazol-4-yl | |
| 16.102 | C₂H₅ | thiazol-4-yl | |
| 16.103 | C₂H₅ | 2-methylthiazol-4-yl | |
| 16.104 | C₂H₅ | thiazol-5-yl | |
| 16.105 | C₂H₅ | 4-methylthiazol-5-yl | |
| 16.106 | C₂H₅ | 2-methylthiazol-5-yl | |
| 16.107 | C₂H₅ | thiazol-2-yl | |
| 16.108 | C₂H₅ | isoxazol-3-yl | |
| 16.109 | C₂H₅ | isoxazol-5-yl | |
| 16.110 | C₂H₅ | isoxazol-4-yl | |
| 16.111 | C₂H₅ | 3-methylisoxazol-5-yl | |
| 16.112 | C₂H₅ | 5-methylisoxazol-3-yl | |
| 16.113 | C₂H₅ | 3,5-dimethylisoxazol-4-yl | |
| 16.114 | C₂H₅ | isothiazol-3-yl | |
| 16.115 | C₂H₅ | isothiazol-4-yl | |
| 16.116 | C₂H₅ | isothiazol-5-yl | |
| 16.117 | C₂H₅ | 3-methylisothiazol-4-yl | |
| 16.118 | C₂H₅ | 3-methylisothiazol-5-yl | |
| 16.119 | C₂H₅ | 1,2,4-triazol-3-yl | |
| 16.120 | C₂H₅ | 1,3,4-oxadiazol-2-yl | |
| 16.121 | C₂H₅ | 2-methyl-1,3,4-oxadiazol-5-yl | |
| 16.122 | C₂H₅ | 1,3,4-thiadiazol-2-yl | |
| 16.123 | C₂H₅ | 2-methyl-1,3,4-thiadiazol-5-yl | |
| 16.124 | C₂H₅ | 1,2,3-thiadiazol-5-yl | |
| 16.125 | C₂H₅ | 1,2,3-thiadiazol-4-yl | |
| 16.126 | C₂H₅ | 5-methyl-1,2,3-thiadiazol-4-yl | |
| 16.127 | C₂H₅ | 1,2,5-thiadiazol-3-yl | |
| 16.128 | C₂H₅ | 3-methyl-1,2,5-thiadiazol-4-yl | |
| 16.129 | C₂H₅ | 1,2,4-thiadiazol-5-yl | |
| 16.130 | C₂H₅ | 1,2,4-thiadiazol-3-yl | |
| 16.131 | C₂H₅ | 1,2,4-oxadiazol-3-yl | |
| 16.132 | C₂H₅ | 1,2,4-oxadiazol-5-yl | |
| 16.133 | C₂H₅ | 1,2,5-oxadiazol-3-yl | |
| 16.134 | C₂H₅ | 3-methyl-1,2,5-oxadiazol-4-yl | |
| 16.135 | C₂H₅ | 1,2,3-triazol-4-yl | |
| 16.136 | C₂H₅ | 1-methyl-1H-1,2,3-triazol-4-yl | |

TABLE 16-continued

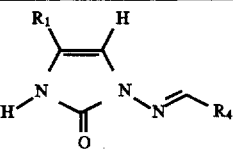

| Compound No. | R₁ | R₄ | Physical Data |
|---|---|---|---|
| 16.137 | C₂H₅ | 4-methyl-1,2,3-triazol-5-yl | |
| 16.138 | C₂H₅ | pyridazin-3-yl | |
| 16.139 | C₂H₅ | 4-methylpyridazin-3-yl | |
| 16.140 | C₂H₅ | pyridazin-4-yl | |
| 16.141 | C₂H₅ | 3-methylpyridazin-4-yl | |
| 16.142 | C₂H₅ | 4-methylpyridazin-5-yl | |
| 16.143 | C₂H₅ | 2-methylpyrimid-5-yl | |
| 16.144 | C₂H₅ | 2,4,6-trimethylpyrimid-5-yl | |
| 16.145 | C₂H₅ | pyrimid-4-yl | |
| 16.146 | C₂H₅ | 4-methylpyrimid-6-yl | |
| 16.147 | C₂H₅ | 2,4-dimethylpyrimid-6-yl | |
| 16.148 | C₂H₅ | pyrimid-2-yl | |
| 16.149 | C₂H₅ | 4,6-dimethylpyrimid-2-yl | |
| 16.150 | C₂H₅ | pyrazin-2-yl | |
| 16.151 | C₂H₅ | 2-methylpyrazin-3-yl | |
| 16.152 | C₂H₅ | 2-methylpyrazin-5-yl | |
| 16.153 | C₂H₅ | 1,2,4-triazin-5-yl | |
| 16.154 | C₂H₅ | 3-methyl-1,2,4-triazin-5-yl | |
| 16.155 | C₂H₅ | 1,3,5-triazin-2-yl | |
| 16.156 | C₂H₅ | 1,2,4,5-tetrazin-3-yl | |
| 16.157 | C₃H₅(cyclo) | pyrrol-3-yl | |
| 16.158 | C₃H₅(cyclo) | 1-methylpyrrol-3-yl | |
| 16.159 | C₃H₅(cyclo) | pyrrol-2-yl | |
| 16.160 | C₃H₅(cyclo) | 1-methyl-1H-pyrazol-3-yl | |
| 16.161 | C₃H₅(cyclo) | pyrazol-3-yl | |
| 16.162 | C₃H₅(cyclo) | pyrazol-4-yl | |
| 16.163 | C₃H₅(cyclo) | 1-methyl-1H-pyrazol-4-yl | |
| 16.164 | C₃H₅(cyclo) | imidazol-2-yl | |
| 16.165 | C₃H₅(cyclo) | imidazol-4-yl | |
| 16.166 | C₃H₅(cyclo) | 1-methyl-1H-imidazol-4-yl | |
| 16.167 | C₃H₅(cyclo) | 1-methyl-1H-imidazol-5-yl | |
| 16.168 | C₃H₅(cyclo) | 4-methylimidazol-5-yl | |
| 16.169 | C₃H₅(cyclo) | tetrazol-5-yl | |
| 16.170 | C₃H₅(cyclo) | 2-methylimidazol-4-yl | |
| 16.171 | C₃H₅(cyclo) | 1-methyl-1H-tetrazol-5-yl | |
| 16.172 | C₃H₅(cyclo) | 2-methyloxazol-5-yl | |
| 16.173 | C₃H₅(cyclo) | 2,4-dimethyloxazol-5-yl | |
| 16.174 | C₃H₅(cyclo) | 2,5-dimethyloxazol-4-yl | |
| 16.175 | C₃H₅(cyclo) | oxazol-5-yl | |
| 16.176 | C₃H₅(cyclo) | oxazol-4-yl | |
| 16.177 | C₃H₅(cyclo) | thiazol-4-yl | |
| 16.178 | C₃H₅(cyclo) | 2-methylthiazol-4-yl | |
| 16.179 | C₃H₅(cyclo) | thiazol-5-yl | |
| 16.180 | C₃H₅(cyclo) | 4-methylthiazol-5-yl | |
| 16.181 | C₃H₅(cyclo) | 2-methylthiazol-5-yl | |
| 16.182 | C₃H₅(cyclo) | thiazol-2-yl | |
| 16.183 | C₃H₅(cyclo) | isoxazol-3-yl | |
| 16.184 | C₃H₅(cyclo) | isoxazol-5-yl | |
| 16.185 | C₃H₅(cyclo) | isoxazol-4-yl | |
| 16.186 | C₃H₅(cyclo) | 3-methylisoxazol-5-yl | |
| 16.187 | C₃H₅(cyclo) | 5-methylisoxazol-3-yl | |
| 16.188 | C₃H₅(cyclo) | 3,5-dimethylisoxazol-4-yl | |
| 16.189 | C₃H₅(cyclo) | isothiazol-3-yl | |
| 16.190 | C₃H₅(cyclo) | isothiazol-4-yl | |
| 16.191 | C₃H₅(cyclo) | isothiazol-5-yl | |
| 16.192 | C₃H₅(cyclo) | 3-methylisothiazol-4-yl | |
| 16.193 | C₃H₅(cyclo) | 3-methylisothiazol-5-yl | |
| 16.194 | C₃H₅(cyclo) | 1,2,4-triazol-3-yl | |
| 16.195 | C₃H₅(cyclo) | 1,3,4-oxadiazol-2-yl | |
| 16.196 | C₃H₅(cyclo) | 2-methyl-1,3,4-oxadiazol-5-yl | |
| 16.197 | C₃H₅(cyclo) | 1,3,4-thiadiazol-2-yl | |
| 16.198 | C₃H₅(cyclo) | 2-methyl-1,3,4-thiadiazol-5-yl | |
| 16.199 | C₃H₅(cyclo) | 1,2,3-thiadiazol-5-yl | |
| 16.200 | C₃H₅(cyclo) | 1,2,3-thiadiazol-4-yl | |
| 16.201 | C₃H₅(cyclo) | 5-methyl-1,2,3-thiadiazol-4-yl | |
| 16.202 | C₃H₅(cyclo) | 1,2,5-thiadiazol-3-yl | |
| 16.203 | C₃H₅(cyclo) | 3-methyl-1,2,5-thiadiazol-4-yl | |
| 16.204 | C₃H₅(cyclo) | 1,2,4-thiadiazol-5-yl | |

TABLE 16-continued $$\underset{H}{\overset{R_1}{\diagup}}C=C\underset{\diagdown}{\overset{H}{\diagup}}$$
(with N-H, C=O, N-N=CH-R₄ structure)

| Compound No. | R₁ | R₄ | Physical Data |
|---|---|---|---|
| 16.205 | C₃H₅(cyclo) | 1,2,4-thiadiazol-3-yl | |
| 16.206 | C₃H₅(cyclo) | 1,2,4-oxadiazol-3-yl | |
| 16.207 | C₃H₅(cyclo) | 1,2,4-oxadiazol-5-yl | |
| 16.208 | C₃H₅(cyclo) | 1,2,5-oxadiazol-3-yl | |
| 16.209 | C₃H₅(cyclo) | 3-methyl-1,2,5-oxadiazol-4-yl | |
| 16.210 | C₃H₅(cyclo) | 1,2,3-triazol-4-yl | |
| 16.211 | C₃H₅(cyclo) | 1-methyl-1H-1,2,3-triazol-4-yl | |
| 16.212 | C₃H₅(cyclo) | 4-methyl-1,2,3-triazol-5-yl | |
| 16.213 | C₃H₅(cyclo) | pyridazin-3-yl | |
| 16.214 | C₃H₅(cyclo) | 4-methylpyridazin-3-yl | |
| 16.215 | C₃H₅(cyclo) | pyridazin-4-yl | |
| 16.216 | C₃H₅(cyclo) | 3-methylpyridazin-4-yl | |
| 16.217 | C₃H₅(cyclo) | 4-methylpridazin-5-yl | |
| 16.218 | C₃H₅(cyclo) | 2-methylpyrimid-5-yl | |
| 16.219 | C₃H₅(cyclo) | 2,4,6-trimethylpyrimid-5-yl | |
| 16.220 | C₃H₅(cyclo) | pyrimid-4-yl | |
| 16.221 | C₃H₅(cyclo) | 4-methylpyrimid-6-yl | |
| 16.222 | C₃H₅(cyclo) | 2,4-dimethylpyrimid-6-yl | |
| 16.223 | C₃H₅(cyclo) | pyrimid-2-yl | |
| 16.224 | C₃H₅(cyclo) | 4,6-dimethylpyrimid-2-yl | |
| 16.225 | C₃H₅(cyclo) | pyrazin-2-yl | |
| 16.226 | C₃H₅(cyclo) | 2-methylpyrazin-3-yl | |
| 16.227 | C₃H₅(cyclo) | 2-methylpyrazin-5-yl | |
| 16.228 | C₃H₅(cyclo) | 1,2,4-triazin-5-yl | |
| 16.229 | C₃H₅(cyclo) | 3-methyl-1,2,4-triazin-5-yl | |
| 16.230 | C₃H₅(cyclo) | 1,3,5-triazin-2-yl | |
| 16.231 | C₃H₅(cyclo) | 1,2,4,5-tetrazin-3-yl | |
| 16.232 | C₃H₅(cyclo) | 3-phenylpyrrol-4-yl | |

TABLE 17

(Structure with R₁, H, N-H, C=O, N-NH-CH₂-R₄)

| Compound No. | R₁ | R₄ | Physical Data |
|---|---|---|---|
| 17.1 | CH₃ | pyraxin-2-yl | |

Formulation Examples (%=per cent by weight)

| Example F1: Emulsion concentrates | a) | b) | c) |
|---|---|---|---|
| Active ingredient No. 4.1 | 25% | 40% | 50% |
| Calcium dodecylbenzenesulfonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

An emulsion concentrate which upon dilution with water gives emulsions of any desired concentration is obtained by mixing freely ground active ingredient and additives.

| Example F2: Solutions | a) | b) | c) | d) |
|---|---|---|---|---|
| Active ingredient No. 9.2 | 80% | 10% | 5% | 95% |
| Ethylene glycol monomethyl ether | 20% | — | — | — |
| Polyethylene glycol (MW 400) | — | 70% | — | — |
| N-Methylpyrrolid-2-one | — | 20% | — | — |
| Epoxidized coconut oil | — | — | 1% | 5% |
| Petroleum ether (boiling range: 160–190°) | — | — | 94% | — |

A solution which is suitable for use in the form of microdrops is obtained by mixing freely ground active ingredient and additives.

| Example F3: Granules | a) | b) | c) | d) |
|---|---|---|---|---|
| Active ingredient No. 4.15 | 5% | 10% | 8% | 21% |
| Kaolin | 94% | — | 79% | 54% |
| Highly-disperse silica | 1% | — | 13% | 7% |
| Attapulgite | — | 90% | — | 18% |

The active ingredient is dissolved in dichloromethane, the solvent is sprayed onto the carrier mixture, and the solvent is evaporated in vacuo.

| Example F4: Dusts | a) | b) |
|---|---|---|
| Active ingredient No. 4.1 | 2% | 5% |
| Highly-disperse silica | 1% | 5% |
| Talc | 97% | — |
| Kaolin | — | 90% |

Ready-to-use dusts are obtained by mixing active ingredient and carriers.

| Example F5: Wettable Powders | a) | b) | c) |
|---|---|---|---|
| Active ingredient No. 9.2 | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of EO) | — | 2% | — |
| Highly-disperse silica | 5% | 10% | 10% |
| Kaolin | 62% | 27% | — |

Active ingredient and additives are mixed, and the mixture is ground on a suitable mill. This gives wettable powders which can be diluted with water to give suspensions of any desired concentration.

| Example F6: Emulsion concentrate | |
|---|---|
| Active ingredient No. 4.15 | 10% |
| Octylphenol polyethylene glycol ether (4–5 mol of EO) | 3% |
| Calcium dodecylbenzenesulfonate | 3% |
| Castor oil polyethylene glycol ether (36 mol of EO) | 4% |
| Cyclohexanone | 30% |
| Xylene mixture | 50% |

An emulsion concentrate, which upon dilution with water gives emulsions of any desired concentration, is obtained by mixing finely ground active ingredient and additives.

| Example F7: Dusts | a) | b) |
| --- | --- | --- |
| Active ingredient No. 9.2 | 5% | 8% |
| Talc | 95% | — |
| Kaolin | — | 92% |

Ready-to-use dusts are obtained by mixing active ingredient and carrier and grinding the mixture on a suitable mill.

| Example F8: Extruder granules | |
| --- | --- |
| Active ingredient No. 4.1 | 10% |
| Sodium liposulfonate | 2% |
| Carboxymethylcellulose | 1% |
| Kaolin | 87% |

Active ingredient and additives are mixed, the mixture is ground, moistened with water, extruded and granulated, and the granules are dried in a stream of air.

| Example F9: Coated granules | |
| --- | --- |
| Active ingredient No. 4.15 | 3% |
| Polyethylene glycol (MW 200) | 3% |
| Kaolin | 94% |

In a mixer, kaolin, which has been moistened with polyethylene glycol, is coated uniformly with the finely ground active ingredient, giving dust-free coated granules.

| Example F10: Suspension concentrate | |
| --- | --- |
| Active ingredient No. 4.15 | 40% |
| Ethylene glycol | 10% |
| Nonylphenol polyethylene glycol ether (15 mol of EO) | 6% |
| Sodium lignosulfonate | 10% |
| Carboxymethylcellulose | 1% |
| Aqueous formaldehyde solution (37%) | 0.2% |
| Aqueous silicone oil emulsion (75%) | 0.8% |
| Water | 32% |

A suspension concentrate, which, upon dilution with water gives suspensions of any desired concentration, is obtained by mixing finely ground active ingredient and additives.

Biological Examples (%=per cent by weight unless otherwise indicated)

Example B1: Activity against *Aphis craccivora*

Pea seedlings are infected with *Aphis craccivora*, subsequently sprayed with a spray mixture comprising 400 ppm of active ingredient and then incubated at 20° C. The test is evaluated after 3 and 6 days. The percentage reduction in population (% activity) is determined by comparing the number of dead aphids on the treated and untreated plants. In this test, compounds of tables 3 to 17 exhibit good activity. In particular, compounds nos. 4.1, 4.15 and 9.2 exhibit an activity of over 80%.

Example B2: Activity against *Bemisia tabaci*

Dwarf bean plants are placed into gauze cages and populated with adult *Bemisia tabaci*. After oviposition, all adults are removed. 10 days later, the plants together with the nymphs are sprayed with an aqueous emulsion spray mixture comprising 400 ppm of the active ingredient After a further 14 days, the percentage hatching rate of the eggs is evaluated by comparison with untreated control batches. In this test, compounds of tables 3 to 17 exhibit good activity.

Example B3: Activity against *Myzus persicae*

Pea seedlings are infected with *Myzus persicae*, subsequently sprayed with a spray mixture comprising 400 ppm of active ingredient and then incubated at 20°. The test is evaluated after 3 and 6 days. The percentage reduction in population (% activity) is determined by comparing the number of dead aphids on the treated and untreated plants.

In this test, compounds of tables 3 to 17 exhibit good activity. In particular, compounds nos. 4.15 and 9.2 exhibit an activity of over 80%.

Example B4: Activity against *Myzus persicae* (systemic)

Pea seedlings are infected with *Myzus persicae*, subsequently placed with their roots into a spray mixture comprising 400 ppm of active ingredient and then incubated at 20°. The test is evaluated after 3 and 6 days. The percentage reduction in population (% activity) is determined by comparing the number of dead aphids on the treated and untreated plants.

In this test, compounds of tables 3 to 17 exhibit good activity. In particular, compounds nos. 4.1, 4.15 and 9.2 exhibit an activity of over 80%.

Example B5: Activity against *Nephotettix cincticeps*

Rice plants are sprayed with an aqueous emulsion spray mixture comprising 400 ppm of active ingredient. After the spray coating has dried on, the plants are populated with larvae in the 2nd and 3rd stages. The test is evaluated after 21 days. The percentage reduction in population (% activity) is determined by comparing the number of surviving leaf hoppers on the treated and untreated plants.

In this test, compounds of tables 3 to 17 exhibit good activity.

Example B6: Activity against *Nephotettix cincticeps* (systemic)

Pots containing rice plants are placed into an aqueous emulsion solution comprising 400 ppm of active ingredient. The plants are subsequently populated with larvae in the 2nd and 3rd stages. The test is evaluated after 6 days. The percentage reduction in population (% activity) is determined by comparing the number of leaf hoppers on the treated and untreated plants.

In this test, compounds of tables 3 to 17 exhibit good activity. In particular, compounds nos. 4.1, 4.15 and 9.2 exhibit an activity of over 80%.

Example B7: Activity against *Nilaparvata lugens*

Rice plants are sprayed with an aqueous emulsion spray mixture comprising 400 ppm of active ingredient. After the spray coating has dried on, the plants are populated with plant hopper larvae in the 2nd and 3rd stages. The test is evaluated after 21 days. The percentage reduction in population (% activity) is determined by comparing the number of surviving plant hoppers on the treated and untreated plants.

In this test, compounds of tables 3 to 17 exhibit good activity. In particular, compounds nos. 4.1, 4.15 and 9.2 exhibit an activity of over 80%.

Example B8: Activity against *Nilaparvata lugens* (systemic)

Pots containing rice plants are placed into an aqueous emulsion solution comprising 400 ppm of active ingredient. The plants are subsequently populated with larvae in the 2nd and 3rd stages. The test is evaluated after 6 days. The percentage reduction in population (% activity) is determined by comparing the number of plant hoppers on the treated and untreated plants.

In this test, compounds of tables 3 to 17 exhibit good activity. In particular, compounds nos. 4.1, 4.15 and 9.2 exhibit an activity of over 80%.

What is claimed is:

1. A compound of the formula

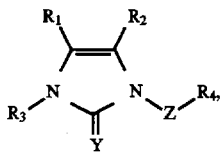

in which $R_1$ and $R_2$, independently of one another, are hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, or unsubstituted or mono-, di- or tri-substituted $C_3$–$C_6$cycloalkyl, substituents being selected from the group consisting of halogen and $C_1$–$C_3$alkyl;

$R_3$ is hydrogen, halo-$C_1$–$C_5$alkyl, N—$C_1$–$C_5$alkyl-N—$C_1$–$C_5$alkoxy-aminocarbonyl, unsubstituted or mono-, di- or tri-substituted $C_1$–$C_5$alkyl, substituents being selected from the group consisting of cyano, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, $C(=O)OR_6$, $C(=O)N(R_7)R_8$, $C(=O)R_9$, $C(O)SR_{10}$, $N(R_{11})R_{12}$, $N=C(H)R_{13}$ or mono-substituted $C_1$–$C_5$alkyl, the substituent being selected from the group consisting of $C(=O)OR_6$, $C(=O)N(R_7)R_8$, $C(=O)R_9$, $C(=O)SRt_{10}$, $N(R_{11})R_{12}$ and $N=C(H)R_{13}$;

$R_4$ is a monocyclic heterocyclic radical, which is unsubstituted or carries from 1 up to and including 3 substituents $R_5$, and where the basic ring structure of $R_4$ has 5 ring members of which from 1 up to and including 4 ring members are hetero atoms of which at least one is an N atom and the remaining hetero atoms, independently of one another, can be N, O or S atoms or has 6 ring members of which from 1 up to and including 4 ring members are N atoms or has 6 ring members of which 1 ring member is a group

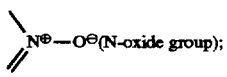

the substituents $R_5$, independently of one another, are halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl, mercapto or phenyl;

$R_6$, $R_7$, $R_8$, $R_9$, $R_{10}$ and $R_{11}$, independently of one another, are hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, or unsubstituted or mono-, di- or tri-substituted $C_3$–$C_6$cycloalkyl, substituents being selected from the group consisting of halogen and $C_1$–$C_3$alkyl;

$R_{12}$ is hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, unsubstituted or mono-, di- or tri-substituted phenyl, substituents being selected from the group consisting of halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl and mercapto, or unsubstituted or in the phenyl moiety mono-, di- or tri-substituted benzyl, substituents being selected from the group consisting of halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl and mercapto;

$R_{13}$ is unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, or an unsubstituted or mono-, di- or tri-substituted phenyl or pyridyl group, substituents being selected from the group consisting of halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl and mercapto;

Y is O, S or $NR_{14}$;

$R_{14}$ is hydrogen, unsubstituted or mono-, di- or tri-substituted $C_1$–$C_5$alkyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkenyl, substituents being selected from the group consisting of halogen, hydroxyl, $C_1$–$C_3$alkoxy and $C_1$–$C_3$alkylthio, unsubstituted or mono-, di- or tri-substituted $C_2$–$C_5$alkynyl, substituents being selected from the group consisting of halogen, $C_1$–$C_3$alkoxy and $C_1$–$C_3$alkylthio, unsubstituted or mono-, di- or tri-substituted $C_3$–$C_6$cycloalkyl, substituents being selected from the group consisting of halogen and $C_1$–$C_3$alkyl, unsubstituted or mono-, di- or tri-substituted phenyl, substituents being selected from the group consisting of halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl and mercapto, or unsubstituted or in the phenyl moiety mono-, di- or tri-substituted benzyl, substituents being selected from the group consisting of halogen, $C_1$–$C_3$alkyl, $C_1$–$C_3$alkoxy, amino, $C_1$–$C_3$alkylamino, di($C_1$–$C_3$)alkylamino, $C_1$–$C_3$alkylthio, hydroxyl and mercapto;

—Z—R$_4$ is —N=C(R$_{15}$)—R$_4$ or —N(R$_{16}$)—C(H)(R$_{15}$)—R$_4$; and

R$_{15}$ and R$_{16}$, independently of one another, are hydrogen or C$_1$–C$_5$alkyl, or, if appropriate, a tautomer thereof, in each case in free form or in salt form.

2. A compound according to claim 1 of the formula I, in which R$_4$ is a pyridyl or 1-oxidopyridinio radical, which radical is unsubstituted or carries from 1 up to and including 2 substituents R$_5$, or, if appropriate, a tautomer thereof.

3. A compound according to claim 1 of the formula I, in which Y is O, or, if appropriate, a tautomer thereof.

4. A compound according to claim 1 of the formula I, in which —Z—R$_4$ is —N=C(H)—R$_4$, or, if appropriate, a tautomer thereof.

5. A compound according to claim 1 of the formula I, in which R$_1$ is hydrogen, unsubstituted or mono- or di-substituted C$_1$–C$_5$alkyl, substituents being selected from the group consisting of C$_1$–C$_3$alkoxy and C$_1$–C$_3$alkylthio, or unsubstituted C$_3$–C$_6$cycloalkyl, R$_2$ is hydrogen, unsubstituted C$_1$–C$_5$alkyl or unsubstituted or mono- or di-substituted C$_2$–C$_5$alkenyl, substituents being selected from the group consisting of halogen, R$_3$ is hydrogen; halo-C$_1$–C$_5$alkyl; N—C$_1$–C$_5$alkyl-N—C$_1$–C$_5$alkoxy-aminocarbonyl; unsubstituted or mono-, di- or tri-substituted C$_1$–C$_5$alkyl, substituents being selected from the group consisting of cyano, C$_1$–C$_3$alkoxy and C$_1$–C$_3$alkylthio; unsubstituted or mono- or di-substituted C$_2$–C$_5$alkenyl, substituents being selected from the group consisting of halogen; unsubstituted C$_2$–C$_5$alkynyl; unsubstituted C$_3$–C$_6$cycloalkyl; C(=O)OR$_6$ wherein R$_6$ is unsubstituted C$_1$–C$_5$alkyl; C(=O)N(R$_7$)R$_8$ wherein R$_7$ and R$_8$, independently of one another, are unsubstituted C$_1$–C$_5$alkyl; C(=O)R$_9$ wherein R$_9$ is unsubstituted or mono- or di-substituted C$_1$–C$_5$alkyl, substituents being selected from the group consisting of C$_1$–C$_3$alkoxy; N=C(H)R$_{13}$ wherein R$_{13}$ is unsubstituted phenyl or unsubstituted pyridyl; or mono-substituted C$_1$–C$_5$alkyl, the substituent being selected from the group consisting of C(=O)OR$_6$ and C(=O)R$_9$ wherein R$_6$ and R$_9$ are unsubstituted C$_1$–C$_5$alkyl, R$_4$ is a pyridyl or 1-oxidopyridinio radical, which radical is unsubstituted or carries from 1 up to and including 2 substituents R$_5$, the substituents R$_5$, independently of one another, are halogen, C$_1$–C$_3$alkyl or phenyl;

Y is O; and

—Z—R$_4$ is —N=C(H)—R$_4$ or —N(H)—C(H)(H)—R$_4$, or, if appropriate, a tautomer thereof.

6. A compound according to claim 5 of the formula I, in which R$_1$ is hydrogen, unsubstituted C$_1$–C$_5$alkyl or unsubstituted cyclopropyl;

R$_2$ is hydrogen, unsubstituted C$_1$–C$_4$alkyl or unsubstituted or mono-substituted C$_3$–C$_4$alkenyl, substituents being selected from the group consisting of halogen;

R$_3$ is hydrogen; N—C$_1$–C$_2$alkyl-N—C$_1$–C$_2$alkoxy-aminocarbonyl; unsubstituted or mono- or di-substituted C$_1$–C$_5$alkyl, substituents being selected from the group consisting of cyano and C$_1$–C$_3$alkoxy; unsubstituted or mono-substituted C$_2$–C$_5$alkenyl, substituents being selected from the group consisting of halogen; unsubstituted C$_3$–C$_5$alkynyl; unsubstituted C$_3$–C$_5$cycloalkyl; C(=O)OR$_6$ wherein R$_6$ is unsubstituted C$_1$–C$_3$alkyl; C(=O)N(R$_7$)R$_8$ wherein R$_7$ and R$_8$, independently of one another, are unsubstituted C$_1$–C$_2$alkyl; C(=O)R$_9$ wherein R$_9$ is unsubstituted or mono-substituted C$_1$–C$_4$alkyl, substituents being selected from the group consisting of C$_1$–C$_2$alkoxy; or mono-substituted C$_1$–C$_5$alkyl, the substituent being selected from the group consisting of C(=O)OR$_6$ and C(=O)R$_9$ wherein R$_6$ and R$_9$ are unsubstituted C$_1$–C$_3$alkyl;

R$_4$ is an unsubstituted pyridyl radical;

Y is O; and

—Z—R$_4$ is —N=C(H)—R$_4$, or, if appropriate, a tautomer thereof.

7. A compound according to claim 6 of the formula I, in which R$_1$ is tert-butyl or methyl;

R$_2$ is hydrogen;

R$_3$ is hydrogen, unsubstituted C$_1$–C$_3$alkyl or C(=O)R$_9$ wherein R$_9$ is unsubstituted C$_1$–C$_3$alkyl;

R$_4$ is an unsubstituted pyridyl radical;

Y is O; and

—Z—R$_4$ is —N=C(H)—R$_4$, or, if appropriate, a tautomer thereof.

8. A compound according to claim 7 of the formula I, in which R$_1$ is methyl, R$_2$ is hydrogen, R$_3$ is C(=O)CH$_3$, Y is O, —Z—R$_4$ is —N=C(H)—R$_4$ and R$_4$ is unsubstituted pyrid-3-yl.

9. A pesticidal composition, which comprises, together with at least one auxiliary, as active ingredient a pesticidally effective mount of at least one compound as claimed in claim 1 of the formula I or, if appropriate, a tautomer thereof, in each case in free form or in agrochemically utilisable salt form.

10. A composition as claimed in claim 9 for controlling insects.

11. A method of controlling pests, which comprises applying a pesticidally effective amount of a composition as claimed in claim 9 to the pests or to their environment.

12. A method as claimed in claim 11 for controlling insects.

13. A method as claimed in claim 11 for the protection of plant propagation material, which comprises treating the propagation material or the locus where the propagation material is planted.

* * * * *